(12) United States Patent
Quail et al.

(10) Patent No.: US 6,858,429 B2
(45) Date of Patent: Feb. 22, 2005

(54) UNIVERSAL LIGHT-SWITCHABLE GENE PROMOTER SYSTEM

(75) Inventors: Peter H. Quail, Vacaville, CA (US); Enamul Huq, El Sobrante, CA (US); James Tepperman, Oakland, CA (US); Sae Sato, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 250 days.

(21) Appl. No.: 10/227,035

(22) Filed: Aug. 23, 2002

(65) Prior Publication Data

US 2003/0082809 A1 May 1, 2003

Related U.S. Application Data

(60) Provisional application No. 60/355,402, filed on Feb. 6, 2002, and provisional application No. 60/314,615, filed on Aug. 23, 2001.

(51) Int. Cl.$^7$ .......................... C12N 1/00; C12N 1/13; C12N 1/19; C12N 5/10; C12N 15/63
(52) U.S. Cl. ............... 435/375; 435/254.11; 435/254.2; 435/257.2; 435/320.1; 435/325; 435/419
(58) Field of Search .............................. 435/375, 320.1, 435/325, 419, 254.11, 257.2, 254.2

(56) References Cited

U.S. PATENT DOCUMENTS 5,283,173 A 2/1994 Fields et al.

OTHER PUBLICATIONS

Barak, S., et al., "All in Good Time: the *Arabidopsis* Circadian Clock", Trends in Plant Science Rev. 5(12)517–522 (2000).
Correll, M.J., et al., "Interactions Between Gravitropism and Phototropism in Plants", J. of Plant Growth Reg. (2002), 8 unnumbered pages.
Fairchild, C. D., et al., "HFR1 encodes an atypical bHLH protein that acts in phytochrome a signal transduction", Genes & Devel. 14:2377–2391 (2000).
Martinez–Garcia, J., et al., "Direct Targeting of Light Signals to a Promoter Element–Bound Transcription Factor", Science, 288:859–863 (2000).
Kim, Lana, et al., "Light–Induced Nuclear Import Of Phytochrome–A:GFP Fusion Proteins Is Differently Regulated In Transgenic Tobacco And Arabidopsis", The Plant Journal, 22(2):125–133 (2000).

Lin, C., "Photoreceptors and Regulation of Flowering Time", Plant Phys. 123:39–50 (2000).
Miller, A., "Clock proteins: Turned over after hours?", Dispatch R529 Current Biol. 10(14), 3 unnumbered pages.
Nagi, F., et al., "Phytochromes pif3 and light signalling go nuclear", Trends in Plant Science–Research News 4(4):125–126 (1999).
Ni, Min, et al., "PIF3, a Phytochrome–Interacting Factor Necessary for Normal Photoinduced Signal Transduction, is a Novel Basic Helix–Loop–Helix Protein", Cell 95:657–667 (1998).
Ni, Min, et al. "Binding of Phytochrome B to its Nuclear Signalling Partner PIF3 is Reversibly Induced by Light", Nature 400:781–784 (1999).
Quail, P., "Phytochrome–interacting Factors", Cell & Devel. Biol. 11:457–466 (2000).
Quail, P., "Phytochrome Photosensory Signaling Networks", Nature Rev. 3:85–93 (2002).
Santelli, R., et al., "A Search For Homologues Of Plant Photoreceptor Genes And Their Signaling Partners In The Sugarcane Expressed Sequence Tag (Sucest) Database", Genetics and Molecular Biol. 24(1–4):49–53 (2001).
Smith, H., "Phytochromes and Light Signal Perception by Plants—An Emerging Synthesis", Nature 407:585–591 (2000).
Yamaguchi, R., et al., "Light–Dependent Translocation of a Phytochrome B–GFP Fusion Protein to the Nucleus in Transgenic *Arabidopsis*", J. of Cell Biol. 145(3):437–445 (1999).
Zhu, Yuxian, et al., "Phytochrome B binds with greater apparent affinity than pytochrome A to the basic helix–loop–helix factor PIF3 in a reaction requiring the PAS domain of PIF3", PNAS Early Edition 1–6 (2000).

*Primary Examiner*—Terry McKelvey
(74) *Attorney, Agent, or Firm*—Morrison & Foerster LLP

(57) ABSTRACT

An artificial promoter system that can be fused upstream of any desired gene enabling reversible induction or repression of the expression of the gene at will in any suitable host cell or organisms by light is described. The design of the system is such that a molecule of the plant photoreceptor phytochrome is targeted to the specific DNA binding site in the promoter by a protein domain that is fused to the phytochrome and that specifically recognizes this binding site. This bound phytochrome, upon activation by light, recruits a second fusion protein consisting of a protein that binds to phytochrome only upon light activation and a transcriptional activation domain that activates expression of the gene downstream of the promoter.

33 Claims, 5 Drawing Sheets

SEQUENCE LISTING

```
<160> NUMBER OF SEQ ID NOS: 11
<210> SEQ ID NO 1
<211> LENGTH: 1172
<212> TYPE: PRT
<213> ORGANISM: Arabidopsis thaliana

<400> SEQUENCE: 1

Met Val Ser Gly Val Gly Gly Ser Gly Gly Arg Gly Gly Gly Arg
 1               5                  10                  15

Gly Gly Glu Glu Glu Pro Ser Ser His Thr Pro Asn Asn Arg Arg
                20                  25                  30

Gly Gly Glu Gln Ala Gln Ser Ser Gly Thr Lys Ser Leu Arg Pro Arg
                35                  40                  45

Ser Asn Thr Glu Ser Met Ser Lys Ala Ile Gln Gln Tyr Thr Val Asp
    50                  55                  60

Ala Arg Leu His Ala Val Phe Glu Gln Ser Gly Glu Ser Gly Lys Ser
65                  70                  75                  80

Phe Asp Tyr Ser Gln Ser Leu Lys Thr Thr Thr Tyr Gly Ser Ser Val
                85                  90                  95

Pro Glu Gln Gln Ile Thr Ala Tyr Leu Ser Arg Ile Gln Arg Gly Gly
                100                 105                 110

Tyr Ile Gln Pro Phe Gly Cys Met Ile Ala Val Asp Glu Ser Ser Phe
            115                 120                 125

Arg Ile Ile Gly Tyr Ser Glu Asn Ala Arg Glu Met Leu Gly Ile Met
        130                 135                 140

Pro Gln Ser Val Pro Thr Leu Glu Lys Pro Glu Ile Leu Ala Met Gly
145                 150                 155                 160

Thr Asp Val Arg Ser Leu Phe Thr Ser Ser Ser Ile Leu Leu Glu
                165                 170                 175

Arg Ala Phe Val Ala Arg Glu Ile Thr Leu Leu Asn Pro Val Trp Ile
                180                 185                 190

His Ser Lys Asn Thr Gly Lys Pro Phe Tyr Ala Ile Leu His Arg Ile
            195                 200                 205

Asp Val Gly Val Val Ile Asp Leu Glu Pro Ala Arg Thr Glu Asp Pro
        210                 215                 220

Ala Leu Ser Ile Ala Gly Ala Val Gln Ser Gln Lys Leu Ala Val Arg
225                 230                 235                 240

Ala Ile Ser Gln Leu Gln Ala Leu Pro Gly Gly Asp Ile Lys Leu Leu
                245                 250                 255

Cys Asp Thr Val Val Glu Ser Val Arg Asp Leu Thr Gly Tyr Asp Arg
                260                 265                 270

Val Met Val Tyr Lys Phe His Glu Asp Glu His Gly Glu Val Val Ala
```

-continued

```
                275                 280                 285
Glu Ser Lys Arg Asp Asp Leu Glu Pro Tyr Ile Gly Leu His Tyr Pro
290                 295                 300

Ala Thr Asp Ile Pro Gln Ala Ser Arg Phe Leu Phe Lys Gln Asn Arg
305                 310                 315                 320

Val Arg Met Ile Val Asp Cys Asn Ala Thr Pro Val Leu Val Val Gln
                325                 330                 335

Asp Asp Arg Leu Thr Gln Ser Met Cys Leu Val Gly Ser Thr Leu Arg
                340                 345                 350

Ala Pro His Gly Cys His Ser Gln Tyr Met Ala Asn Met Gly Ser Ile
            355                 360                 365

Ala Ser Leu Ala Met Ala Val Ile Ile Asn Gly Asn Glu Asp Asp Gly
370                 375                 380

Ser Asn Val Ala Ser Gly Arg Ser Ser Met Arg Leu Trp Gly Leu Val
385                 390                 395                 400

Val Cys His His Thr Ser Ser Arg Cys Ile Pro Phe Pro Leu Arg Tyr
                405                 410                 415

Ala Cys Glu Phe Leu Met Gln Ala Phe Gly Leu Gln Leu Asn Met Glu
                420                 425                 430

Leu Gln Leu Ala Leu Gln Met Ser Glu Lys Arg Val Leu Arg Thr Gln
            435                 440                 445

Thr Leu Leu Cys Asp Met Leu Leu Arg Asp Ser Pro Ala Gly Ile Val
            450                 455                 460

Thr Gln Ser Pro Ser Ile Met Asp Leu Val Lys Cys Asp Gly Ala Ala
465                 470                 475                 480

Phe Leu Tyr His Gly Lys Tyr Tyr Pro Leu Gly Val Ala Pro Ser Glu
                485                 490                 495

Val Gln Ile Lys Asp Val Val Glu Trp Leu Leu Ala Asn His Ala Asp
                500                 505                 510

Ser Thr Gly Leu Ser Thr Asp Ser Leu Gly Asp Ala Gly Tyr Pro Gly
            515                 520                 525

Ala Ala Ala Leu Gly Asp Ala Val Cys Gly Met Ala Val Ala Tyr Ile
530                 535                 540

Thr Lys Arg Asp Phe Leu Phe Trp Phe Arg Ser His Thr Ala Lys Glu
545                 550                 555                 560

Ile Lys Trp Gly Gly Ala Lys His His Pro Glu Asp Lys Asp Asp Gly
                565                 570                 575

Gln Arg Met His Pro Arg Ser Ser Phe Gln Ala Phe Leu Glu Val Val
                580                 585                 590

Lys Ser Arg Ser Gln Pro Trp Glu Thr Ala Glu Met Asp Ala Ile His
            595                 600                 605

Ser Leu Gln Leu Ile Leu Arg Asp Ser Phe Lys Glu Ser Glu Ala Ala
            610                 615                 620

Met Asn Ser Lys Val Val Asp Gly Val Val Gln Pro Cys Arg Asp Met
625                 630                 635                 640

Ala Gly Glu Gln Gly Ile Asp Glu Leu Gly Ala Val Ala Arg Glu Met
                645                 650                 655

Val Arg Leu Ile Glu Thr Ala Thr Val Pro Ile Phe Ala Val Asp Ala
                660                 665                 670

Gly Gly Cys Ile Asn Gly Trp Asn Ala Lys Ile Ala Glu Leu Thr Gly
            675                 680                 685

Leu Ser Val Glu Glu Ala Met Gly Lys Ser Leu Val Ser Asp Leu Ile
690                 695                 700
```

-continued

```
Tyr Lys Glu Asn Glu Ala Thr Val Asn Lys Leu Leu Ser Arg Ala Leu
705                 710                 715                 720

Arg Gly Asp Glu Glu Lys Asn Val Glu Val Lys Leu Lys Thr Phe Ser
                725                 730                 735

Pro Glu Leu Gln Gly Lys Ala Val Phe Val Val Asn Ala Cys Ser
                740                 745                 750

Ser Lys Asp Tyr Leu Asn Asn Ile Val Gly Val Cys Phe Val Gly Gln
                755                 760                 765

Asp Val Thr Ser Gln Lys Ile Val Met Asp Lys Phe Ile Asn Ile Gln
                770                 775                 780

Gly Asp Tyr Lys Ala Ile Val His Ser Pro Asn Pro Leu Ile Pro Pro
785                 790                 795                 800

Ile Phe Ala Ala Asp Glu Asn Thr Cys Cys Leu Glu Trp Asn Met Ala
                805                 810                 815

Met Glu Lys Leu Thr Gly Trp Ser Arg Ser Glu Val Ile Gly Lys Met
                820                 825                 830

Ile Val Gly Glu Val Phe Gly Ser Cys Cys Met Leu Lys Gly Pro Asp
                835                 840                 845

Ala Leu Thr Lys Phe Met Ile Val Leu His Asn Ala Ile Gly Gly Gln
850                 855                 860

Asp Thr Asp Lys Phe Pro Phe Pro Phe Phe Asp Arg Asn Gly Lys Phe
865                 870                 875                 880

Val Gln Ala Leu Leu Thr Ala Asn Lys Arg Val Ser Leu Glu Gly Lys
                885                 890                 895

Val Ile Gly Ala Phe Cys Phe Leu Gln Ile Pro Ser Pro Glu Leu Gln
                900                 905                 910

Gln Ala Leu Ala Val Gln Arg Arg Gln Asp Thr Glu Cys Phe Thr Lys
                915                 920                 925

Ala Lys Glu Leu Ala Tyr Ile Cys Gln Val Ile Lys Asn Pro Leu Ser
                930                 935                 940

Gly Met Arg Phe Ala Asn Ser Leu Leu Glu Ala Thr Asp Leu Asn Glu
945                 950                 955                 960

Asp Gln Lys Gln Leu Leu Glu Thr Ser Val Ser Cys Glu Lys Gln Ile
                965                 970                 975

Ser Arg Ile Val Gly Asp Met Asp Leu Glu Ser Ile Glu Asp Gly Ser
                980                 985                 990

Phe Val Leu Lys Arg Glu Glu Phe Phe Leu Gly Ser Val Ile Asn Ala
                995                 1000                1005

Ile Val Ser Gln Ala Met Phe Leu Leu Arg Asp Arg Gly Leu Gln Leu
    1010                1015                1020

Ile Arg Asp Ile Pro Glu Glu Ile Lys Ser Ile Glu Val Phe Gly Asp
1025                1030                1035                1040

Gln Ile Arg Ile Gln Gln Leu Leu Ala Glu Phe Leu Leu Ser Ile Ile
                1045                1050                1055

Arg Tyr Ala Pro Ser Gln Glu Trp Val Glu Ile His Leu Ser Gln Leu
                1060                1065                1070

Ser Lys Gln Met Ala Asp Gly Phe Ala Ala Ile Arg Thr Glu Phe Arg
    1075                1080                1085

Met Ala Cys Pro Gly Glu Gly Leu Pro Pro Glu Leu Val Arg Asp Met
    1090                1095                1100

Phe His Ser Ser Arg Trp Thr Ser Pro Glu Gly Leu Gly Leu Ser Val
1105                1110                1115                1120
```

```
Cys Arg Lys Ile Leu Lys Leu Met Asn Gly Glu Val Gln Tyr Ile Arg
            1125                1130                1135

Glu Ser Glu Arg Ser Tyr Phe Leu Ile Ile Leu Glu Leu Pro Val Pro
        1140                1145                1150

Arg Lys Arg Pro Leu Ser Thr Ala Ser Gly Ser Gly Asp Met Met Leu
        1155                1160                1165

Met Met Pro Tyr
    1170

<210> SEQ ID NO 2
<211> LENGTH: 524
<212> TYPE: PRT
<213> ORGANISM: Arabidopsis thaliana

<400> SEQUENCE: 2

Met Pro Leu Phe Glu Leu Phe Arg Leu Thr Lys Ala Lys Leu Glu Ser
  1               5                  10                  15

Ala Gln Asp Arg Asn Pro Ser Pro Val Asp Glu Val Val Glu Leu
            20                  25                  30

Val Trp Glu Asn Gly Gln Ile Ser Thr Gln Ser Gln Ser Ser Arg Ser
        35                  40                  45

Arg Asn Ile Pro Pro Pro Gln Ala Asn Ser Ser Arg Ala Arg Glu Ile
    50                  55                  60

Gly Asn Gly Ser Lys Thr Thr Met Val Asp Glu Ile Pro Met Ser Val
65                  70                  75                  80

Pro Ser Leu Met Thr Gly Leu Ser Gln Asp Asp Phe Val Pro Trp
                85                  90                  95

Leu Asn His His Pro Ser Leu Asp Gly Tyr Cys Ser Asp Phe Leu Arg
                100                 105                 110

Asp Val Ser Ser Pro Val Thr Val Asn Glu Gln Glu Ser Asp Met Ala
            115                 120                 125

Val Asn Gln Thr Ala Phe Pro Leu Phe Gln Arg Arg Lys Asp Gly Asn
    130                 135                 140

Glu Ser Ala Pro Ala Ala Ser Ser Ser Gln Tyr Asn Gly Phe Gln Ser
145                 150                 155                 160

His Ser Leu Tyr Gly Ser Asp Arg Ala Arg Asp Leu Pro Ser Gln Gln
                165                 170                 175

Thr Asn Pro Asp Arg Phe Thr Gln Thr Gln Glu Pro Leu Ile Thr Ser
            180                 185                 190

Asn Lys Pro Ser Leu Val Asn Phe Ser His Phe Leu Arg Pro Ala Thr
        195                 200                 205

Phe Ala Lys Thr Thr Asn Asn Asn Leu His Asp Thr Lys Glu Lys Ser
    210                 215                 220

Pro Gln Ser Pro Pro Asn Val Phe Gln Thr Arg Val Leu Gly Ala Lys
225                 230                 235                 240

Asp Ser Glu Asp Lys Val Leu Asn Glu Ser Val Ala Ser Ala Thr Pro
                245                 250                 255

Lys Asp Asn Gln Lys Ala Cys Leu Ile Ser Glu Asp Ser Cys Arg Lys
            260                 265                 270

Asp Gln Glu Ser Glu Lys Ala Val Val Cys Ser Ser Val Gly Ser Gly
        275                 280                 285

Asn Ser Leu Asp Gly Pro Ser Glu Ser Pro Ser Leu Ser Leu Lys Arg
    290                 295                 300

Lys His Ser Asn Ile Gln Asp Ile Asp Cys His Ser Glu Asp Val Glu
305                 310                 315                 320
```

```
Glu Glu Ser Gly Asp Gly Arg Lys Glu Ala Gly Pro Ser Arg Thr Gly
            325                 330                 335

Leu Gly Ser Lys Arg Ser Arg Ser Ala Glu Val His Asn Leu Ser Glu
            340                 345                 350

Arg Arg Arg Arg Asp Arg Ile Asn Glu Lys Met Arg Ala Leu Gln Glu
            355                 360                 365

Leu Ile Pro Asn Cys Asn Lys Val Asp Lys Ala Ser Met Leu Asp Glu
        370                 375                 380

Ala Ile Glu Tyr Leu Lys Ser Leu Gln Leu Gln Val Gln Ile Met Ser
385                 390                 395                 400

Met Ala Ser Gly Tyr Tyr Leu Pro Ala Val Met Phe Pro Pro Gly
                405                 410                 415

Met Gly His Tyr Pro Ala Ala Ala Ala Met Ala Met Gly Met Gly
                420                 425                 430

Met Pro Tyr Ala Met Gly Leu Pro Asp Leu Ser Arg Gly Gly Ser Ser
            435                 440                 445

Val Asn His Gly Pro Gln Phe Gln Val Ser Gly Met Gln Gln Gln Pro
        450                 455                 460

Val Ala Met Gly Ile Pro Arg Val Ser Gly Gly Ile Phe Ala Gly
465                 470                 475                 480

Ser Ser Thr Ile Gly Asn Gly Ser Thr Arg Asp Leu Ser Gly Ser Lys
                485                 490                 495

Asp Gln Thr Thr Thr Asn Asn Asn Ser Asn Leu Lys Pro Ile Lys Arg
            500                 505                 510

Lys Gln Gly Ser Ser Asp Gln Phe Cys Gly Ser Ser
            515                 520

<210> SEQ ID NO 3
<211> LENGTH: 439
<212> TYPE: PRT
<213> ORGANISM: Arabidopsis thaliana

<400> SEQUENCE: 3

Met Val Thr Leu Thr Pro Ser Ser Ala Ser Thr Pro Lys Thr Ser Phe
 1               5                  10                  15

Asp Phe Met Lys Asn Asn Ser His Ser Ser Leu Tyr Val Ser Ser
            20                  25                  30

Ser Tyr Leu Ser Ser Lys Glu Asp Ala Leu Val Thr Thr Lys Lys
        35                  40                  45

Leu Met Glu Pro Ser Lys Thr Leu Asn Met Ser Ile Asn Pro Lys Gln
50                  55                  60

Glu Glu Phe Gly Asp Glu Lys Lys Met Val Lys Lys Ala Pro Glu Asp
65                  70                  75                  80

Pro Glu Ile Gly Val Phe Gly Ala Glu Lys Tyr Phe Asn Gly Asp Met
                85                  90                  95

Asp Ser Asp Gln Gly Ser Ser Val Leu Ser Leu Thr Asn Pro Glu Val
            100                 105                 110

Glu Arg Thr Val Val Asp Ser Lys Gln Ser Ala Lys Lys Ser Thr Gly
            115                 120                 125

Thr Pro Ser Val Arg Ser Glu Ser Ser Trp Asn Ser Gln Ser Val Leu
        130                 135                 140

Leu Gln Asn Lys Leu Val Asn Ser Cys Asn Ser Ser Phe Lys Glu Lys
145                 150                 155                 160

Lys Asn Ser Asn Gly Gln Ile Gln Lys Val Thr Asn Asn Lys Lys Ser
```

-continued

```
                        165                 170                 175
Phe Leu Ala Asn Leu Gly Cys Lys Cys Ala Cys Ser Asp Gly Asp Ser
                    180                 185                 190
Val Asp Val Asp Glu Lys Thr Ser Val Lys Arg Ser Ala Asp Pro Asn
                195                 200                 205
Ile Ser Val Ile Thr Met Arg Ser Ser Ala Asp Met Asn Thr Glu Leu
            210                 215                 220
Ile Lys Ile Gln Lys Gln Glu Leu Ser Gln Arg Lys Ser Leu Glu
225                 230                 235                 240
Val Phe Gly Ser Pro Val Ala Ile Glu Lys Lys Ser Ser Val Val Gln
                245                 250                 255
Lys Lys Leu Pro Leu Pro Pro Trp Lys Ser Arg Thr Glu Glu Asp Asp
                260                 265                 270
Thr Lys Ser Glu Gly Ser Asp Ser Ser Asp Leu Phe Glu Ile Glu
            275                 280                 285
Gly Leu Thr Gly Asn Pro Lys Pro Phe Leu Thr Arg Gln Gly Ser Asp
    290                 295                 300
Pro Ala Ser Pro Thr Cys Tyr Ala Pro Ser Glu Val Ser Val Glu Trp
305                 310                 315                 320
Ser Ile Val Thr Ala Ser Ala Asp Phe Ser Val Met Ser Glu Cys
                325                 330                 335
Ala Thr Ser Pro Val Arg Arg Asn Arg Pro Thr Gln Ile Pro Arg Ile
                340                 345                 350
Pro Ile Thr Ala Lys Ser Ala Pro Gln Arg Arg Lys Ser Ser Ser Ser
            355                 360                 365
Ser Gly Gly Asn Gly Phe Leu Met Ser Cys Lys Ser His Lys Ser Val
    370                 375                 380
Met Val Ser Gly Asp Leu Asp Arg Arg Ser Ser Met Asn Lys Thr Gln
385                 390                 395                 400
Pro Ser Tyr Val Pro Arg Phe Pro Met Glu Thr Thr Lys Pro Lys Ser
                405                 410                 415
Phe Glu Thr Arg Arg Arg Ile Ser Asn Ser Ser Ile Ser His Thr Gln
                420                 425                 430
Ser Ser Leu Leu Tyr Ser Gln
            435

<210> SEQ ID NO 4
<211> LENGTH: 231
<212> TYPE: PRT
<213> ORGANISM: Arabidopsis thaliana

<400> SEQUENCE: 4

Met Val Gly Ala Thr Val Val Ser Lys Trp Thr Pro Leu Cys Val Ala
1               5                   10                  15
Ser Pro Pro Glu Arg Asn Ser Ala Ser Leu Asn Pro His Cys Ser Pro
                20                  25                  30
Ala Arg Val Asn Phe Arg Thr Ala Leu Ala Ala Phe Arg Pro Gln Phe
            35                  40                  45
Arg Leu Phe Ser Arg Asn Ser Ala Ser Arg Arg Leu Arg Ala Ser
    50                  55                  60
Ser Ser Ala Glu Ser Gly Ile Phe Leu Pro His Leu Val Ala Ser Met
65                  70                  75                  80
Glu Asp Val Glu Glu Thr Tyr Ile Met Val Lys Pro Asp Gly Ile Gln
                85                  90                  95
```

```
Arg Gly Leu Val Gly Glu Ile Ile Ser Arg Phe Glu Lys Lys Gly Phe
            100                 105                 110

Lys Leu Ile Gly Leu Lys Met Phe Gln Cys Pro Lys Glu Leu Ala Glu
            115                 120                 125

Glu His Tyr Lys Glu Leu Ser Ala Lys Ser Phe Phe Leu Thr Leu Ile
            130                 135                 140

Glu Tyr Ile Thr Ser Gly Pro Val Val Cys Met Ala Trp Glu Gly Val
145                 150                 155                 160

Gly Val Val Ala Ser Ala Arg Lys Leu Ile Gly Lys Thr Asp Pro Leu
                165                 170                 175

Gln Ala Glu Pro Gly Thr Ile Arg Gly Asp Leu Ala Val Gln Thr Gly
            180                 185                 190

Arg Asn Ile Val His Gly Ser Asp Ser Pro Glu Asn Gly Lys Arg Glu
            195                 200                 205

Ile Gly Leu Trp Phe Lys Glu Gly Leu Cys Lys Trp Asp Ser Ala
            210                 215                 220

Leu Ala Thr Trp Leu Arg Glu
225                 230

<210> SEQ ID NO 5
<211> LENGTH: 430
<212> TYPE: PRT
<213> ORGANISM: Arabidopsis thaliana

<400> SEQUENCE: 5

Met Glu His Gln Gly Trp Ser Phe Glu Glu Asn Tyr Ser Leu Ser Thr
  1               5                  10                  15

Asn Arg Arg Ser Ile Arg Pro Gln Asp Glu Leu Val Glu Leu Leu Trp
             20                  25                  30

Arg Asp Gly Gln Val Val Leu Gln Ser Gln Thr His Arg Glu Gln Thr
         35                  40                  45

Gln Thr Gln Lys Gln Asp His His Glu Leu Ala Leu Arg Ser Ser Thr
     50                  55                  60

Phe Leu Glu Asp Gln Glu Thr Val Ser Trp Ile Gln Tyr Pro Pro Asp
65                  70                  75                  80

Glu Asp Pro Phe Glu Pro Asp Asp Phe Ser His Phe Phe Ser Thr
                 85                  90                  95

Met Asp Pro Leu Gln Arg Pro Thr Ser Glu Thr Val Lys Pro Lys Ser
            100                 105                 110

Ser Pro Glu Pro Pro Gln Val Met Val Lys Pro Lys Ala Cys Pro Asp
            115                 120                 125

Pro Pro Pro Gln Val Met Pro Pro Lys Phe Arg Leu Thr Asn Ser
            130                 135                 140

Ser Ser Gly Ile Arg Glu Thr Glu Met Glu Gln Tyr Ser Val Thr Thr
145                 150                 155                 160

Val Gly Pro Ser His Cys Gly Ser Asn Pro Ser Gln Asn Asp Leu Asp
                165                 170                 175

Val Ser Met Ser His Asp Arg Ser Lys Asn Ile Glu Glu Lys Leu Asn
            180                 185                 190

Pro Asn Ala Ser Ser Ser Gly Gly Ser Ser Gly Cys Ser Phe Gly
            195                 200                 205

Lys Asp Ile Lys Glu Met Ala Ser Gly Arg Cys Ile Thr Thr Asp Arg
    210                 215                 220

Lys Arg Lys Arg Ile Asn His Thr Asp Glu Ser Val Ser Leu Ser Asp
225                 230                 235                 240
```

```
Ala Ile Gly Asn Lys Ser Asn Gln Arg Ser Gly Ser Asn Arg Ser
            245                 250                 255

Arg Ala Ala Glu Val His Asn Leu Ser Glu Arg Arg Arg Asp Arg
            260                 265                 270

Ile Asn Glu Arg Met Lys Ala Leu Gln Glu Leu Ile Pro His Cys Ser
            275                 280                 285

Lys Thr Asp Lys Ala Ser Ile Leu Asp Glu Ala Ile Asp Tyr Leu Lys
            290                 295                 300

Ser Leu Gln Leu Gln Leu Gln Val Met Trp Met Gly Ser Gly Met Ala
305                 310                 315                 320

Ala Ala Ala Ser Ala Pro Met Met Phe Pro Gly Val Gln Pro Gln
            325                 330                 335

Gln Phe Ile Arg Gln Ile Gln Ser Pro Val Gln Leu Pro Arg Phe Pro
            340                 345                 350

Val Met Asp Gln Ser Ala Ile Gln Asn Asn Pro Gly Leu Val Cys Gln
            355                 360                 365

Asn Pro Val Gln Asn Gln Ile Ile Ser Asp Arg Phe Ala Arg Tyr Ile
            370                 375                 380

Gly Gly Phe Pro His Met Gln Ala Ala Thr Gln Met Gln Pro Met Glu
385                 390                 395                 400

Met Leu Arg Phe Ser Ser Pro Ala Gly Gln Gln Ser Gln Gln Pro Ser
            405                 410                 415

Ser Val Pro Thr Lys Thr Thr Asp Gly Ser Arg Leu Asp His
            420                 425                 430

<210> SEQ ID NO 6
<211> LENGTH: 27
<212> TYPE: DNA
<213> ORGANISM: Artificial Sequence
<220> FEATURE:
<223> OTHER INFORMATION: Primer

<400> SEQUENCE: 6
ggggatccaa tgtcaggctc taggccg                                    27

<210> SEQ ID NO 7
<211> LENGTH: 28
<212> TYPE: DNA
<213> ORGANISM: Artificial Sequence
<220> FEATURE:
<223> OTHER INFORMATION: Primer

<400> SEQUENCE: 7
cccccgggta cttgtttgct gcagcgag                                   28

<210> SEQ ID NO 8
<211> LENGTH: 44
<212> TYPE: DNA
<213> ORGANISM: Artificial Sequence
<220> FEATURE:
<223> OTHER INFORMATION: Primer

<400> SEQUENCE: 8
tataagaaga ggcggccgca aatggtttcc ggagtcgggg gtag                 44

<210> SEQ ID NO 9
<211> LENGTH: 45
<212> TYPE: DNA
<213> ORGANISM: Artificial Sequence
<220> FEATURE:
```

```
<223> OTHER INFORMATION: Primer

<400> SEQUENCE: 9
tataagaaga ggcggccgca aagattcttt aaaagagtct ctcag          45

<210> SEQ ID NO 10
<211> LENGTH: 44
<212> TYPE: DNA
<213> ORGANISM: Artificial Sequence
<220> FEATURE:
<223> OTHER INFORMATION: Primer

<400> SEQUENCE: 10
tataagaaga ggcggccgca aatggtttcc ggagtcgggg gtag           44

<210> SEQ ID NO 11
<211> LENGTH: 43
<212> TYPE: DNA
<213> ORGANISM: Artificial Sequence
<220> FEATURE:
<223> OTHER INFORMATION: Primer

<400> SEQUENCE: 11
tataagaaga ggcggccgca aatatggcat catcagcatc atg            43
```

UNIVERSAL LIGHT-SWITCHABLE GENE PROMOTER SYSTEM

RELATED APPLICATIONS

This application claims priority to U.S. Application Ser. No. 60/355,402 filed Feb. 6, 2002, and U.S. Application Ser. No. 60/314,615 filed Aug. 23, 2001, both of which are hereby incorporated by reference in their entirety.

This invention was funded by grant number DE-FG03-87ER13742 from the Department of Energy; grant number 5335-2100-006-010 from the United States Department of Agriculture and grant number GM 47475 from the National Institutes of Health. The U.S. Government may have certain rights to this invention.

FIELD OF THE INVENTION

This invention is in the field of molecular biology. In particular, this invention relates to an artificial promoter system that can be fused upstream of any desired gene enabling reversible induction or repression of the gene at will in any suitable host cell or organism by light.

BACKGROUND OF THE INVENTION

There is a general need for readily regulatable promoters to control gene expression in a variety of experimental and commercial applications. Currently, the majority of such systems that have been developed are based on the administration of chemical effectors which require diffusion into the cell to provide appropriate, non-toxic concentrations of chemical at the target-gene site. This can be problematic, because of the potential for toxic, unintended or pleiotropic effects of the inducing chemical, and especially in multicellular organisms, where synchronous spatial and temporal induction or repression of target gene expression is desired in all cells. There is thus a tremendous need to develop an artificial promoter system that can be fused upstream of any desired gene enabling reversible induction or repression of the expression of the gene at will in any suitable host cell or organisms by light.

SUMMARY OF THE INVENTION

In order to meet these needs, the present invention is directed to an artificial promoter system that can be fused upstream of any desired gene enabling reversible induction or repression of the expression of the gene at will in any suitable host cell or organisms by light. We describe here a gene promoter system which has all the desirable advantages of an inducible system, such as, low background activity (negligible basal expression in the absence of the inducer), high inducibility, noninvasive inducibility, switchable, inducible at a similar level in any tissue or organism; rapid, reversible, dose-dependent, gene-specific induction of expression upon administration of the inducer; inexpensive; non-toxic; accurately dosable, lacking pleiotropic and unintended effects, simple to administer, and combinable with cell or tissue specific expression.

The design of the system is such that a molecule of the plant photoreceptor phytochrome is targeted to the specific DNA binding site in the promoter of a desired gene by a protein domain that is fused to the phytochrome and that specifically recognizes this binding site. This bound phytochrome, upon activation by light, recruits a second fusion protein including a protein that binds to phytochrome only upon light activation and a transcriptional regulatory protein with a transcriptional activation or repressor domain that activates or represses expression of the gene downstream of the promoter.

The system enables essentially instantaneous, noninvasive, switchable control of any desired gene in any suitable cell. The gene may be recombinant or naturally occurring within the cell. Such cells include, but are not limited to, plant, algae, fungi (yeast) and animal (mammals including humans, insects, worms, fish), simply by administration of appropriate light to those cells. The system of the invention may produce any desired level of product with a single short pulse of light given at time zero. As short as 10 seconds of a moderate intensity light (50 micromols/m$^2$/s) is enough to saturate the system completely. This can be decreased to a 1 second flash with a high intensity light source such as a light-emitting-diode (LED) array, or a laser. No further light is needed again after that first pulse. The system of the invention provides "dial-a-level" of gene expression with exquisite precision by dialing in the light intensity and time of the pulse. The invention can be automated and/or scaled up.

In the system of the invention, the level of expression in the dark in cells is quantitatively indistinguishable from the background controls. That is, the promoter system is very "tight" in the uninduced state, a highly desirable feature in practice.

The level of expression in the system is induced over 1000-fold by a single pulse of red light. Such red light will have a wavelength peak maximum of 665 nm. Thus the system has a very robust degree of inducibility over a large dynamic range, also a very desirable feature.

The red light induced increase in expression is completely abrogated by an immediately subsequent far-red pulse showing that the system can be switched off completely, back down to the background control levels. Such far-red light will have a wavelength peak maximum of 730–760 nm. The level of induction is quite respectable in absolute terms compared to a very strong activator, another feature important in practical terms.

In one format, the present invention is directed to a cell wherein the cell contains (1) a target gene; (2) a phytochrome-DNA-binding-domain fusion protein (PDBP); (3) a phytochrome-interacting factor (PIF)-activation domain fusion protein (PIF-AD) and (4) a chromophore. The target gene can be produced recombinantly. Alternatively, the target gene may be naturally occurring from the cell. The chromophore can be produced recombinantly. Alternatively, the chromophore can be exogenously supplied. In some cells, the chromophore may be produced naturally.

The present invention is further directed to isolated DNA constructs selected from (1) a target gene DNA construct; (2) a DNA construct encoding a phytochrome-DNA-binding-domain fusion protein (PDBP); (3) a DNA construct encoding a phytochrome-interacting factor (PIF)-activation domain fusion protein (PIF-AD) and (4) a DNA construct encoding a chromophore biosynthetic protein or proteins.

The present invention is further directed to a cell wherein the cell contains (1) a target gene or a target gene DNA construct; (2) a DNA construct encoding a phytochrome-DNA-binding-domain fusion protein (PDBP); (3) a DNA construct encoding a phytochrome-interacting factor (PIF)-activation domain fusion protein (PIF-AD) or a phytochrome-interacting factor (PIF)-repressor domain fusion protein (PIF-RD) and (4) a DNA construct encoding a chromophore biosynthetic protein or proteins.

In one embodiment, the target-gene is naturally present in the cell of interest and comprises a basal gene promoter that has a specific DNA sequence that can bind a specific cognate protein domain. The gene to be regulated is generally located downstream from the promoter.

In another embodiment, the target-gene construct comprises a basal gene promoter into which a specific DNA sequence that can bind a specific cognate protein domain has been inserted. Downstream of the promoter, the construct comprises a gene of choice whose expression it is desired to regulate. These embodiments are illustrated in FIGS. 1A–1B. In another embodiment, the construct encoding the phytochrome-DNA-binding-domain fusion protein (PDBP) includes a chimeric gene encoding a phytochrome polypeptide fused in-frame to a protein domain that binds specifically to the cognate binding-site DNA sequence inserted into the promoter of the target-gene construct of the invention. This gene is fused to a promoter suitable for driving expression in the selected host cell or organism as illustrated in FIG. 1A.

In a further embodiment, the construct encoding the phytochrome-interacting factor (PIF)-activation domain fusion protein (PIF-AD) includes a chimeric gene encoding a phytochrome-interacting protein fused in-frame to a transcriptional activation domain. This gene is fused to a promoter suitable for driving expression in the selected host cell or organism as illustrated in FIGS. 1A–1B.

In one embodiment, the chromophore is a tetrapyrrole chromophore capable of attachment to the phytochrome apoprotein to form the photoactive holoprotein photoreceptor supplied to the host cell. In one format, this is accomplished by supplying the chemically-purified chromophore exogenously to the host cells. In another format, this is accomplished by genetically engineering the host cell to synthesize the chromophore endogenously. The latter is done by transforming the host cell to express one or more genes encoding enzymes that convert normal, cellularly available heme to the native chromophore, phytochromobilin.

In one embodiment, the first gene encodes a ferredoxin-dependent heme oxygenase, designated HY1, that converts heme to biliverdin IX-alpha. Genes capable of providing this function have been identified and cloned in *Arabidopsis* Davis,. et al. (1999) Proc. Natl. Acad. Sci. USA 96:6541–6546; Muramoto et al. (1999) Plant Cell 11:335–347 and in the cyanobacterium Synechocystis sp. PCC 6803, Willows et al. (2000) Plant Mol. Biol. 43:113–120. In another embodiment, the second gene encodes phytochromobilin synthase, a ferredoxin-dependent biliverdin reductase, designated HY2, which has been identified and cloned in *Arabidopsis*, Kohchi et al. (2001) Plant Cell 13: 425–436. other plants, and certain bacteria, Frankenberg et al., (2001) Plant Cell 13:965–978.

The invention is further directed to kits containing the DNA constructs of the invention. The kits may include one or more DNA constructs including: (1) a target gene DNA construct; (2) a DNA construct encoding a phytochrome-DNA-binding-domain fusion protein (PDBP); (3) a DNA construct encoding a phytochrome-interacting factor (PIF)-activation domain fusion protein (PIF-AD) or a DNA construct encoding a phytochrome-interacting factor (PIF)-repressor domain fusion protein (PIF-RD) and (4) a DNA construct encoding a chromophore biosynthetic protein or proteins, or chemically purified chromophore or chromophores.

The invention is further directed to methods of using the DNA constructs of the invention to induce or repress a gene in a cell by the use of light. In one embodiment, host cells are genetically transformed, using standard procedures, to contain the target gene construct and to express the phytochrome DNA binding proteins (PDBP) and PIF-AD fusion proteins or PIF-RD fusion proteins. Where desired, these host cells are also transformed to express the necessary enzymes for endogenous chromophore synthesis. Otherwise, chromophore is supplied exogenously in chemically purified form to the host cells.

Alternatively, host cells are selected which contain a target gene of interest. In this embodiment, the host cells are genetically transformed, using standard procedures, to contain the target gene construct and to express the phytochrome DNA binding proteins (PDBP) and PIF-AD fusion proteins or PIF-RD fusion proteins.

In the methods of the invention, cells are maintained in darkness until it is desired to activate the expression of the target gene. In darkness, the PDBP fusion protein is synthesized, and the chromophore is attached to the phytochrome moiety to generate the biologically inactive Pr conformer. This fusion protein will bind to its DNA-binding site in the target gene promoter, via its DNA-binding domain, but because the phytochrome moiety is in the Pr conformer, it will not bind to the PIF-AD protein. In this configuration, the target gene is off. To activate expression of the target gene, cells are exposed to red light. For red light, a wavelength peak maximum ($\lambda_{max}$) of 665 nm with a fluence (dose) 3,000 micromoles per square meter can be utilized. This light wavelength converts the phytochrome moiety generally within one second to the biologically active Pfr conformer of the photoreceptor that binds the PIF moiety of the PIF-AD protein with high affinity. The photoactivated PDBP molecule thereby recruits the PIF-AD protein to the target promoter where the transcriptional activation domain of PIF-AD induces transcription of the target gene. To switch off expression of this gene, cells are exposed to far-red light. For far-red light, a wavelength peak $\lambda_{max}$, 730–760 nm; fluence (dose) 18,000 micromoles per square meter may be utilized. This wavelength of light switches the phytochrome molecule back to the inactive Pr conformer generally within one second causing rapid dissociation of PIF-AD and termination of the transcriptional activation of the target gene. This overall activation-deactivation process can be repeated at will using sequential exposure of cells to red and far-red light.

In an alternative to the transcriptional activation configuration described above, the invention can be configured to provide light-activated transcriptional repression. This is accomplished by (a) substituting a transcriptional repression domain (RD) for the activation domain above, to create a PIF-RD fusion protein; and (b) inserting the DNA-binding sequence for PDBP in a constitutively active promoter to create a repressible-gene construct analogous to, but functionally the converse of, that described above. Appropriately transformed host cells will then constitutively express the target gene in darkness, will repress expression when exposed to red light, and will resume expression upon subsequent exposure to far-red light.

The invention is further directed to a cell having a first recombinant fusion protein including phytochrome and a DNA binding protein and a second recombinant fusion protein including a phytochrome interacting protein and a second DNA binding protein. The cell may further include one or more recombinant chromophore biosynthetic proteins. Alternatively, the cell may further include one or more exogenously supplied chromophores. The cells will include a target gene. The target gene may be naturally present in the cell of interest. Alternatively, the target gene may be introduced into the cell as a recombinant target gene construct.

The cells may be of any type. For example, the cells may be mammalian cells, plant cells or microbial cells. The mammalian cells may be human cells.

In one format, the first and second recombinant fusion proteins may be encoded by the same DNA construct.

The present invention is further directed to a cell having a first recombinant DNA construct encoding phytochrome and a DNA binding protein and a second recombinant DNA construct encoding a phytochrome interacting protein and a transcriptional regulatory protein. The first and said second DNA constructs may be cloned into a single vector or multiple vectors.

In one format, the first and said second DNA constructs further include a promoter active in the cell. In another format, the cell further includes a third DNA construct encoding a chromophore biosynthetic protein. In, yet another format, the cell may further include a fourth DNA construct encoding a target gene.

The present invention is further directed to a kit having a first DNA construct encoding phytochrome and a DNA binding protein and a second DNA construct encoding a phytochrome interacting protein and a transcriptional regulatory protein. In one format of the kit the DNA constructs are cloned into one or more vectors. The kit may further include instructions for use. The kit may also further include a light source or a chromophore. The chromophore may be in the form of a DNA construct encoding a chromophore biosynthetic protein. The kit may also include a construct encoding a target gene.

The present invention is further directed to a composition including a DNA construct encoding phytochrome and a first DNA binding protein and a second DNA construct encoding a phytochrome interacting protein and a second DNA binding protein. The composition may further include a DNA construct encoding one or more chromophore biosynthetic genes. The compositions may further include a target gene construct. In one format of the composition the DNA construct may be cloned into one or more vectors. In one format, the transcriptional regulatory protein is an activator. In another format, it is a repressor.

The present invention is further directed to a method of regulating the expression of a target gene by light by a) incubating a cell having 1) a target gene with a promoter; 2) a phytochrome chromophore; 3) a first recombinant fusion protein including phytochrome with Pr and Pfr conformers and a DNA binding protein and a second recombinant fusion protein including 4) a phytochrome interacting protein and a transcriptional regulatory protein in the dark under conditions so that the chromophore attaches to the phytochrome to generate the Pr conformer and the first DNA binding protein fusion protein binds to its DNA-binding site in the target gene promoter and b) exposing the cell to sufficient light to convert the Pr conformer to the Pfr conformer to thereby permit the phytochrome to bind to the phytochrome interacting protein and allow the transcriptional regulatory protein to regulate the expression of the target gene.

In one format of the method, the transcriptional regulatory protein is an activator. In another format, it is a repressor.

BRIEF DESCRIPTION OF THE DRAWINGS

FIG. 2(A) shows the results of a yeast two-hybrid plate growth assay. FIG. 2(B) shows he results of a yeast two-hybrid quantitative liquid assay.

FIG. 3(A) shows a time-course of reporter-gene expression in yeast cells after various preincubation treatments. FIG. 3(B) shows the effect of duration of red light, irradiation. FIG. 3(C) shows the fluence(dose)-response curve of reporter gene expression in yeast. FIG. 3(D) shows the effect of a far-red light pulse (FRp) in reversing red light pulse-induction (Rp) of gene expression. FIG. 3(E) shows the short-term kinetics of induction, and reversal of induction of gene expression by Rp and FRp light-pulses.

DETAILED DESCRIPTION OF THE INVENTION

Figure 1A:
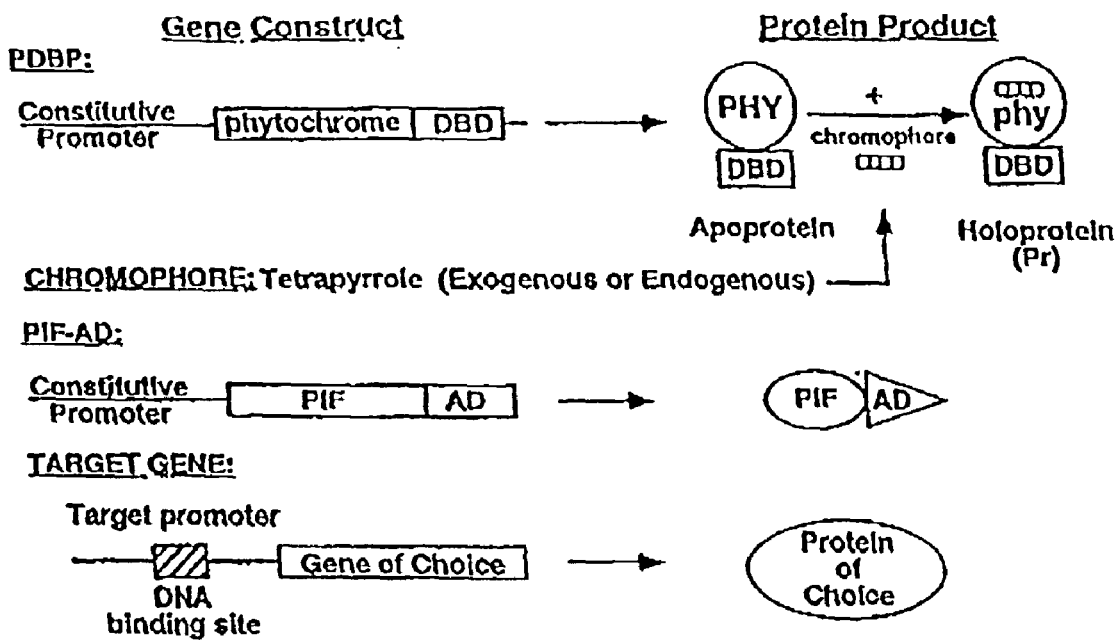
FIG. 1A shows a diagram of the light-switchable promoter system.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, website u.r.l.s, patents and published patent specifications are referenced. The disclosures of these publications, patents and published patent specifications are hereby incorporated by reference into the present disclosure to more fully describe the state of the art to which this invention pertains.

Definitions

The practice of the present invention will employ, unless otherwise indicated, conventional techniques of immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y.

In order to facilitate review of the various embodiments of the invention, the following definitions are provided:

Promoter: A regulatory nucleic acid sequence, typically located upstream (5') of a gene that, in conjunction with various cellular proteins, is responsible for regulating the expression of the gene.

Sequence Identity: As can be appreciated by one of ordinary skill in art, DNA and protein sequences of similar identity find use in the invention so long as they provide the same function of the related sequence to which they share identity. The similarity between two nucleic acid sequences, or two amino acid sequences is expressed in terms of sequence identity (or, for proteins, also in terms of sequence similarity). Sequence identity is frequently measured in terms of percentage identity; the higher the percentage, the more similar the two sequences are.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al., (1988); Huang et al., (1992); and Pearson et al, (1994). Altschul et al., (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the web site ncbi.nlm.nlh.gov/BLAST. A description of how to determine sequence identity using this program is available at the web site nchi.nlm.nih.gov/BLAST/blast.help.

Homologs of the disclosed protein sequences with comparable activity are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. A preferred method utilizes the BLASTN module of WU-BLAST-2 (Altschul et al. 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 90% or at least about 95% sequence identity.

The alignment may include the introduction of gaps in the sequences to be aligned. In addition, for sequences which contain either more or fewer amino acids than the protein encoded by the sequences in the figures, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleotides, frameshifts, unknown nucleotides, or other types of sequencing errors in any of the sequences; however, the correct sequences will fall within the homology and stringency definitions herein.

Vector: A nucleic acid molecule as introduced into a host cell, thereby producing a transformed host cell. A vector may include one or more nucleic acid sequences that permit it to replicate in one or more host cells, such as origin(s) of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into a cell such as plant, algae, fungi (yeast) and animal (mammals, insects, worms, fish), including transfection with viral vectors, transformation by *Agrobacterium*, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below.

Operably Linked: A first nucleic acid sequence is "operably linked" with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell, however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated", as described above.

Naturally Occurring: By "naturally occurring nucleic acid or gene" it is meant a nucleic acid or gene that occurs naturally and is therefore produced endogenously within a cell and is not produced by recombinant means.

Complementary DNA (cDNA): A piece of DNA that is synthesized in the laboratory by reverse transcription of an RNA, preferably an RNA extracted from cells. cDNA produced from mRNA typically lacks internal, non-coding segments (introns) and regulatory sequences that determine transcription.

Open Reading Frame (ORF): A series of nucleotide triplets (codons) coding for amino acids without any internal termination codons. These sequences are usually translatable into a peptide.

Ortholog: Two nucleotide or amino acid sequences are orthologs of each other if they share a common ancestral sequence and diverged when a species carrying that ancestral sequence split into two species, sub-species, or cultivars. Orthologous sequences are also homologous sequences. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

Gene: A "gene" refers to a polynucleotide containing at least one open reading frame that is capable of encoding a particular protein after being transcribed and translated. Such genes may be naturally occurring or recombinant.

Primer: The terms "primer" and "nucleic acid primer" are used interchangeably herein. A "primer" refers to a short polynucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a polymerase and at a suitable temperature and pH. The primer may be either single-stranded or double-stranded and must be sufficiently long to prime the synthesis of the desired extension product. The exact length of the primer will depend upon many factors, including temperature, source of primer and use of the method.

Polymerase Chain Reaction: A "polymerase chain reaction" ("PCR") is a reaction in which replicate copies are made of a target polynucleotide using a "primer pair" or a "set of primers" consisting of an "forward" and a "reverse" primer, and a catalyst of polymerization, such as a DNA polymerase, and particularly a thermally stable polymerase enzyme. Methods for PCR are taught in U.S. Pat. No. 4,683,195 (Mullis) and U.S. Pat. No. 4,683,202 (Mullis et al.). All processes of producing replicate copies of the same polynucleotide, such as PCR or gene cloning, are collectively referred to herein as "amplification" or "replication".

DNA Binding Protein: Any polypeptide that binds a defined DNA sequence can be used as a DNA-binding domain and is defined herein as a "DNA Binding Protein". By a "DNA binding domain" or "DBD", or "DNA Binding Protein" is meant a polypeptide sequence which is capable of directing specific polypeptide binding to a particular DNA sequence (i.e., to a DBD recognition element). The term "domain" in this context is not intended to be limited to a discrete folding domain. Rather, consideration of a polypeptide as a DBD for use can be made simply by the observation that the polypeptide has a specific DNA binding activity.

The DNA-binding domain can carry an "activation" domain or a "repressor" domain.

The DNA-binding domain can be derived from a naturally occurring DNA-binding protein, e.g., a prokaryotic or eukaryotic DNA-binding protein. Alternatively, the DNA-binding domain can be a polypeptide derived from a protein artificially engineered to interact with specific DNA sequences. Examples of DNA-binding domains from naturally occurring eukaryotic DNA-binding proteins include p53, Jun, Fos, GCN4, or GAL4. The DNA-binding domain of the fusion protein can also be generated from viral proteins, such as the pappillomavirus E2 protein. In another example, the DNA-binding domain is derived from a prokaryote, e.g., the E. coli LexA repressor can be used, or the DNA-binding domain can be from a bacteriophage, e.g., a lambda cI protein. Exemplary prokaryotic DNA-binding domains include DNA-binding portions of the P22 Arc repressor, MetJ, CENP-B, Rap1, Xyl1S/Ada/AraC, Bir5 and DtxR. As merely illustrative, the fusion protein can be constructed utilizing the DNA binding portions of the LysR family of transcriptional regulators, e.g., Trp1, HvY, OccR, OxyR, CatR, NahR, MetR, CysB, NodD or SyrM (Schell et al. (1993) Annu Rev Microbiol 47:597), or the DNA binding portions of the PhoB/OmpR-related proteins, e.g., PhoB, OmpR, CacC, PhoM, PhoP, ToxR, VirG or SfrA (Makino et al. (1996) J Mol Biol 259:15), or the DNA binding portions of histones H1 or H5 (Suzuki et al. (1995) FEBS Lett 372:215). Other exemplary DBD's which can be used to generate the fusion protein include DNA binding portions of the P22 Arc repressor, MetJ, CENP-B, Rap1, Xyl1S/Ada/AraC, Bir5 or DtxR. Other exemplary DNA binding proteins include those described in Riechmann, et al. Science 290:2105–2110 such as MYB-(R1) R2R3, AP2/EREBP, bHLH, NAC, C₂H₂(Zn), HB, MADS, bZIP, WRKY(Zn), GARP, Dof(Zn), CO-like(Zn) and GAIA(Zn).

The DNA-binding protein also can be a non-naturally occurring DNA-binding domain and can be generated by combinatorial mutagenic techniques. Methods for generating novel DNA-binding proteins which can selectively bind to a specific DNA sequence are known in the art. See e.g., U.S. Pat. No. 5,198,346.

As appropriate, the DNA binding motif used to generate the DNA binding protein can include oligomerization motifs. As known in the art, certain transcriptional regulators dimerize, with dimerization promoting cooperative binding of the two monomers to their cognate recognition elements. For example, where the protein includes a LexA DNA binding domain, it can further include a LexA dimerization domain; this optional domain facilitates efficient LexA dimer formation. Because LexA binds its DNA binding site as a dimer, inclusion of this domain in the protein also optimizes the efficiency of operator occupancy (Golemis and Brent, (1992) Mol. Cell Biol. 12:3006). Other oligomerization motifs useful in the present invention will be readily recognized by those skilled in the art. Exemplary motifs include the oligomerization domain of lambda, the tetramerization domain of p53 and the tetramerization domain of BCR-ABL. In addition, the art also provides a variety of techniques for identifying other naturally occurring oligomerization domains, as well as oligomerization domains derived from mutant or otherwise artificial sequences. See, for example, Zeng et al. (1997) Gene 185:245.

Transcription Regulatory Protein: As defined herein, the term transcription regulatory protein refers to a protein that does not bind DNA but nevertheless regulates transcription. Transcription regulatory proteins contain repressor or activator domains. A transcription regulatory protein with a repressor domain represses transcription. A transcription regulatory protein with an activator domain activates transcription. The transcriptional regulatory protein may consist solely of an activator or regulatory domain without additional amino acids. Alternatively, the transcriptional regulatory protein may include the activator or regulatory domain along with additional amino acids.

Repressor Domain: The term "repressor domain" refers to a polypeptide sequence which may participate as a component of a transcriptional complex to otherwise repress transcription. Repressor domains are also known as an "inactivation domains" and "suppressor domains". The repressor domain can be a polymerase interaction domain or some other polypeptide sequence which interacts with or is covalently bound to one or more subunits (or a fragment thereof) of a transcriptional complex. Repressor domains can also be sequences derived from repressors sequences. Exemplary but not limiting examples of repressor domains include SSN-6/TUP-, Kruppel-family suppressor domains or Tet repressors such as those described in U.S. Pat. No. 6,242,667.

Activation Domain: The term "activation domain" refers to a polypeptide sequence which participates as a component of a transcriptional complex, or which recruits an active polymerase complex to thereby increase transcription. The activation domain can be a polymerase interaction domain or some other polypeptide sequence which interacts with, or is covalently bound to, one or more subunits (or a fragment thereof) of a transcriptional complex. Activation domains can also be sequences which are derived from, e.g., transcription factors or other proteins which interact, directly or indirectly, with transcriptional complexes. Activation tags can even be from random polypeptide libraries.

Phytochrome: The term phytochrome refers to a family of photosensory molecules that plants and bacteria use to monitor informational light signals in the environment. These molecules, together with other informational photoreceptors, including the cryptochromes and phototropins provide plants and bacteria with the capacity to continuously track the presence, absence, spectral quality, fluence rate, directionality and diurnal duration of incoming light signals, and to adjust their growth and development toward optimal radiant energy capture, survival and reproduction. Acquisition of this photosensory information by the phytochromes is facilitated by the capacity of the photoreceptor molecule to undergo light-induced, reversible interconversion between two forms: The biologically inactive Pr form which absorbs red (R) photons most efficiently ($\lambda_{max}$, 665 nm), and the biologically active Pfr form which absorbs far red (FR) photons most efficiently ($\lambda_{max}$, 730 nm). Pfr formation (signal perception) initiates a cellular transduction process that culminates in altered expression of selected genes responsible for directing morphogenesis appropriate for the prevailing conditions, whereas reconversion to Pr can abrogate this process. The generic phytochrome molecule is a soluble dimer of two ~125 kD polypeptides, each of which folds into two major structural domains: an N-terminal domain that cradles a single, covalently attached tetrapyrrole chromophore, phytochromobilin; and a C-terminal domain that mediates dimerization. An exemplary phytochrome sequence is as follows with the invariant residues marked in bold font.

MVSGVGGSGGGRGGGRGGEEEPSSSHTP-
NNRRGGEQAQSSGTKSLRPRSNTESMSKAI
QQYTVDARLHAVFEQSGESGKSFDYSQS-
LKTTTYGSSVPEQQITAYLSRIQRGGYIQPF
GCMIAVDESSFRIIGYSENAREMLGIMPQSVPTLEK-
PEILAMGTDVRSLFTSSSSILLERAF VAREI TLLN-
PVWIHSKNTGKPFYAILHRIDVGVVIDLEP
ARTEDPALSIAGAVQ-SQKLA VRAISQLQALPG-
GDIKLLCDTVVESVRDLTGYDRVMVYKF-
HEDEHGEVVAESKRDDLE PYIGLHYPATDIPQASR-
FLFKQNRVRMIVDCNATPVLVVQDDRLTQSMC
LVGSTLRA PHGCHSQYMANMGSIASLAMAVI-
INGNEDDGSNVASGRSSMRLWGLVVCHHTSSRC
IPFPLRYACEFLMQAFGLQLNMELQLA-
LQMSEKRVLRTQTLLCDMLLRDSPAGIVTQS PSIM-
DLVKCDGAAFLYHGKYYPLGVAPSEV-
QIKDVVEWLLANHADSTGLSTDSLGDAG
YPGAAALGDAVCGMAVAYITKRDFLFW-
FRSHTAKEIKWGGAKHHPEDKDDGQRMHP RSS-
FQAFLEVVKSRSQPWETAEMDAIHSLQ-
LILRDSFKESEAAMNSKVVDGVVQPCRD
MAGEQGIDELGAVAREMVRLIETATVPI-
FAVDAGGCINGWNAKIAELTGLSVEEAMG KSLVS-
DLIYKENEATVNKLLSRALRGDEEKN-
VEVKLKTFSPELQGKAVFVVVNACSSKDY
LNNIVGVCFVGQDVTSQKIVMDKFIN-
IQGDYKAIVHSPNPLIPPIFAADENTCCLEWNM
AMEKLTGWSRSEVIGKMIVGEVFGSCCM-
LKGPDALTKFMIVLHNAIGGQDTDKFPFPFF
DRNGKFVQALLTANKRVSLEGKVIGAFC-
FLQIPSPELQQALAVQRRQDTECFTKAKELAYI
CQVIKNPLSGMRFANSLLEAT-
DLNEDQKQLLETSVSCEKQISRIVGD-
MDLESIEDGSFVL KREEFFLGSVINAIVSQAMFLL-
RDRGLQLIRDIPEEIKSIEVFGDQIRIQQLLAEFLL
SIIRYA PSQEWVEIHLSQLSKQMADGFAAIRTE-
FRMACPGEGLPPELVRDMFHSSRWTSPEGLGL

SVCRKILKLMNGEVQYIRESERSYFLI-ILELPVPRKRPLSTASGSGDMMLMMPY (SEQ ID NO:1)

Phytochrome Interacting Protein: A phytochrome interacting protein (PIF) is a protein that binds to and/or interacts with phytochrome as described in Ni, et al. Cell 95:657–667; Ni, et al. Nature 400:781–784 and Martinez-Garcia, et al. Science 288:859–863. An exemplary, but not limiting example of a phytochrome interacting protein is PIF3 from *Arabidopsis*.

The protein sequence for *Arabidopsis* PIF 3 is as follows:
MPLFELFRLTKAKLESAQDRNPSP-PVDEVVELVWENGQISTQSQSSRSRNIPPPQANSSRAREIGNGSKTTMVDEIPMSVPSLMT-GLSQDDDFVPWLNHHPSLDGYCSDFLRDVSSPVTVNEQESDMAVNQTAFPLFQRRKDGNESA-PAASSSQYNGFQSHSLYGSDRARDLPSQQTNPDRFTQTQEPLITSNKPSLVNFSHFLR-PATFAKTTNNNLHDTKEKSPQSPPNVFQTRVLGAKDSEDKVLNESVASATPKDNQKAC-LISEDSCRKDQESEKAVVCSSVGSGNSLDGPSESPSLSLKRKHSNIQDIDCHSEDVEEES-GDGRKEAGPSRTGLGSKRSRSAE-VHNLSERRRRDR INEKMRALQELIPNCNKVDKASMLDEAIEYLKSL-QLQVQIMSMASGYYLPPA-VMFPPGMG HYPAAAAAMAMGMGMPY-AMGLPDLSRGGSSVNHGPQFQVSGM-QQQPVAMGIPRVSGG hGIFAGSSTIGNGSTRDLSG-SKDQTTTNNNSNLKPIKRKQGSSDQFCGSS (SEQ ID NO:2)

Other PIF protein sequences, as detailed in Quail, Current Opinion in Cell Biology 14:180–188 (2002)), include:
PKS1 (*Arabidopsis thaliana*)
MVTLTPSSASTPKTSFDFMKNNNSHSS-LYVSSSSYLSSKEDALVTTKKLMEPSK TLNMSINP-KQEEFGDEKKMVKKAPEDPEIGVF-GAEKYFNGDMDSDQGSSVLSLTNPEVERTVVDSKQSAKKSTGTPS-VRSESSWNSQSVLLQNKLVNSCNSSFKEK KNSNG-QIQKVTNNKKSFLANLGCKCACSDGDS-VDVDEKTSVKRSADPNISVITMRSSADMNTELIKIQKQEELSQRK-SLEVFGSPVAIEKKSSVVQKKLPLPPWKSRT EED-DTKSEGSDSSSDLFEIEGLTGNPKPFL-TRQGSDPASPTCYAPSEVSVEWSIVTASAADFSVMSECATSPVRRNRPT-QIPRIPITAKSAPQRRKSSSSSGGNGFLM SCKSHKS-VMVSGDLDRRSSMNKTQPSYVPRFP-METTKPKSFETRRRISNSSIS HTQSSLLYSQ (SEQ ID NO:3)

NDPK2 (*Arabidopsis thaliana*)
MVGATVVSKWTPLCVASPPERNSASLN-PHCSPARVNFRTALAAFRPQFRLFSRNSASRRRLRASSSAESGIFLPHLVASMEDVEETY-IMVKPDGIQRGLVGEIISRFEKKGFKLIGLKMFQCPKELAEEHYKELSAKSFFLTLIEYITSG-PVVCMAWEGVGVVASARKLIGKTDPLQAEPGTIRGDLAVQTGRNIVHGSDSPENGKREIGLW-FKEGELCKWDSALATWLRE (SEQ ID NO:4)

PIF4 (*Arabidopsis thaliana*)
MEHQGWSFEENYSLSTNRRSIRPQDELV-ELLWRDGQVVLQSQTHREQTQTQKQDHHEEALRSSTFLEDQETVSWIQYPPDEDPFEP-DDFSSHFFSTMDPLQRPTSETVKPKSSPEPPQVMVKPKACPDPPPQVMPPPKFRLTNSSS-GIRETEMEQYSVTTVGPSHCGSNPSQNDLDVSMSHDRSKNIEEKLNPNASSSSGGSSGCS-FGKDIKEMASGRCITTDRKRKRINHTDESVSLSDAIGNKSNQRSGSNRRSRAAE-VHNLSERRRRDRINERMKALQELIPHC-SKTDKASILDE AIDYLKSLQLQLQVMWMGSGMAAAAASAPM-MFPGVQPQQFIRQIQSPVQLPRF-PVMDQ SAIQNNPGLVCQNPVQNQIIS-DRFARYIGGFPHMQAATQMQPMEMLRF-SSPAGQQSQQ PSSVPTKTTDGSRLDH (SEQ ID NO:5)

Fusion Protein: A fusion protein is a fusion or linkage of two or more different polypeptides. The linked peptides may be joined or linked by a linker peptide. Fusion proteins generally have all or a substantial portion of a first polypeptide linked at the amino(N-) or carboxy(C-) terminus to all or a portion of a second polypeptide.

Chromophore: A chromophore is a light absorbing group that covalently attaches to phytochrome to form the photoactive holoprotein.

Taking into account these definitions, the present invention is directed to an artificial promoter system that can be fused upstream of any target gene enabling reversible induction or repression of the gene at will in any suitable host cell or organisms by light.

Alternatively, any natural, endogenous gene can be brought under light-switchable control of induction or repression using this system, if a promoter element and its cognate DNA-binding protein are known for that endogenous gene. In this case, the DNA-binding domain (DBD) of the endogenous cognate DNA-binding protein is fused to the phytochrome molecule, to produce the phy-DBD fusion protein, analogous to that shown in FIG. 1A, thereby directing the light-switchable components (phy-DBD and PIF-AD) to the natural promoter of the endogenous target gene, in the same manner as for the artificial promoter system.

Examples of the classes of potential target genes (recombinant or naturally occurring) include, but are not limited to, genes involved in growth, development, reproduction, and survival, including genes involved in DNA replication, transcription, translation, transcript and protein processing and turnover, cell-cycle regulation, inter- and intra-cellular signaling, cellular energy production and utilization, and biosynthesis of various molecules, including those providing immunity and resistance, and those useful in therapeutic applications, especially gene therapy.

The target-gene is present in the cell of interest and comprises a basal gene promoter that has a specific DNA sequence that can bind a specific cognate protein domain. The gene to be regulated is generally located downstream from the promoter. The gene may be naturally occurring or be recombinantly produced. Representative target genes of interest include plant genes encoding R proteins, PR proteins, prosystemin, and floral inducers; animal genes encoding cytokines, homeodomain proteins, and cell-cycle regulators; and recombinant genes encoding Cre recombinase, transposons, DTA, and BT toxins.

Figure 1B:
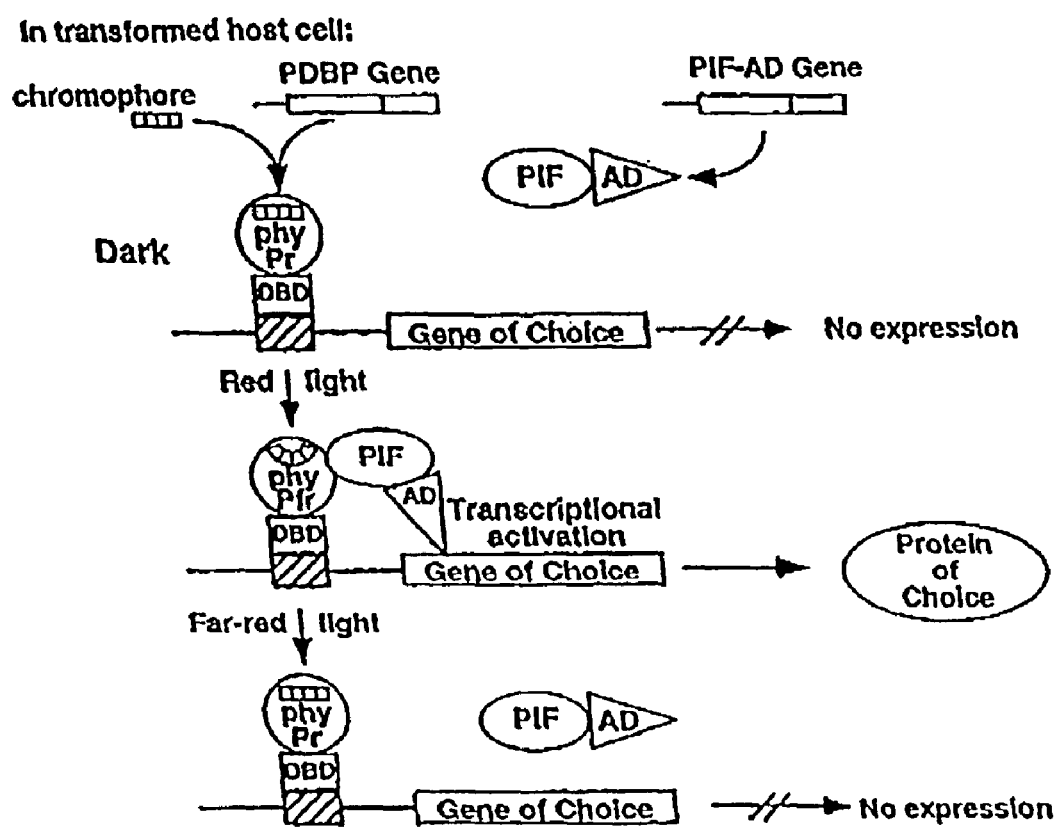
FIG. 1B illustrates a procedure for utilizing the light switchable gene promoter system.

FIGS. 1A–B shows a schematic representation of one format of the light-switchable gene promoter system. In this system, cells transformed with the vectors indicated are maintained in darkness until it is desired to activate the expression of a target gene. In darkness, the phytochrome fusion protein is synthesized, and the chromophore is attached to the phytochrome moiety to generate the biologically inactive Pr conformer. This fusion protein will bind to its DNA-binding site in the target gene promoter, via its DNA-binding domain, but because the phytochrome moiety is in the Pr conformer, it will not bind to the PIF3-AD protein. In this configuration, the target gene is off. To activate expression of the target gene, cells are exposed to red light. This light wavelength converts the phytochrome moiety within one second to the biologically active Pfr conformer of the photoreceptor that binds the PIF3 moiety of the PIF3-AD fusion protein with high affinity. The photoactivated phy(Pfr)-BD molecule thereby recruits the PIF3-AD protein to the target promoter where the transcriptional activation domain of PIF3-AD induces transcription of the target gene. To switch off expression of this gene, cells are exposed to far-red light. This wavelength of light switches the phytochrome molecule back to the inactive Pr conformer within one second causing rapid dissociation of PIF3-AD and termination of the transcriptional activation of the target gene. This overall activation-deactivation process can be repeated at will using sequential exposure of cells to red and far-red light. This system can theoretically function in any cell or organism that can either synthesize the chromophore (PCB) endogenously or take up exogenously supplied PCB. A cell or organism can also be genetically engineered to synthesize PCB and assemble holophytochrome as shown in bacteria.

In another format, the activator may be replaced with a repressor.

Preparation of Gene Constructs

The nucleic acids used in the present invention may be prepared by recombinant nucleic acid methods well known to those of ordinary skill in the art.

1. Target Gene DNA Constructs

The DNA sequences may be derived from a variety of sources, including genomic DNA, subgenomic DNA, cDNA, synthetic DNA, and combinations thereof. Genomic and cDNA may be obtained in a number of ways. Cells coding for the desired sequence may be isolated, the genomic DNA fragmented (e.g., by treatment with one or more restriction endonucleases), and the resulting fragments cloned, identified with a probe complementary to the desired sequence, and screened for the presence of a sequence coding for the desired activity.

For cDNA, the cDNA may be cloned and the resulting clone screened with a probe for cDNA coding for the desired region. Upon isolation of the desired clone, the cDNA may be manipulated in substantially the same manner as the genomic DNA.

To express the DNA sequences, transcriptional and translational signals recognized by an appropriate host are necessary. Alternatively, the promoter region from genomic DNA may be obtained in association with the DNA sequence for the fusion protein. To the extent that the host cells recognize the transcriptional regulatory and translational initiation signals associated with the fusion protein, the 5' region adjacent to the coding sequence may be retained and employed for transcriptional and translational regulation. This region typically will include those sequences involved with initiation of transcription and translation, such as the TATA box, capping sequence, CAAT sequence, and the like. Typically, this region will be at least about 150 base pairs long, more typically about 200 bp, and rarely exceeding about 1 to 2 kb.

The non-coding 3' region may be retained, as well, especially for its transcriptional termination regulatory sequences, such as the stop signal and polyadenylated region. In addition, the non-coding 3' region may also contain an enhancer. Where the transcriptional termination signals are not satisfactorily functional in the host cell, then a functional 3' region from a different gene may be substituted. In this method, the choice of the substituted 3' region would depend upon the cell system chosen for expression.

A wide variety of transcriptional and translational regulatory sequences may be employed, depending upon the nature of the host. The transcriptional and translational regulatory sequences may be derived from viral sources (e.g., adenovirus, bovine papilloma virus, Simian virus, and the like) where the regulatory signals are derived from a gene that has a high level of expression in the host. Alternatively, promoters from mammalian expression products (e.g., actin, collagen, myosin, and the like) may be employed. In another format, the promoter may be from a plant, algae, fungi (yeast), insects, worms or fish.

2. Phytrochrome-DNA Binding Domain Fusion Products

To form the phytochrome-DNA binding domain chimeric gene constructs, DNA fragments may be ligated in accordance with conventional techniques known in the art. Such techniques include use of restriction enzymes to convert sticky-ended fragments to blunt ends (or vice-versa), polymerases and nucleotides to fill in sticky ends to form blunt ends, alkaline phosphatase to avoid undesired ligations, and ligases to join fragments.

The construct for a phytrochrome DNA binding domain-interacting domain may be joined together to form a single DNA segment or may be maintained as separate segments by themselves or in conjunction with vectors. The constructs may be introduced into a cell by transformation in conjunction with a gene allowing for selection where the construct will become integrated into the host genome. Usually, the construct will be part of a vector having a replication system recognized by the host cell. Phytochrome encoding DNA may be from any source including plants and bacteria. Representative phytochrome encoding genes are described in Quail (1998) Phil. Trans. R. Soc. Lond. B, 353:1399–1403. In this invention, phytochrome homologs with as low as 40% or more sequence identity to known phytochromes find use in the invention so long as they can bind chromophores and have phytochrome activity. The DNA-binding domain will generally be cloned from the same cell type as the target gene of interest. However, any DNA binding domain will suffice so long as it binds to the target gene of interest and activates or represses transcription, as desired.

3. Phytochrome-Interacting Factor (PIF)-Activation Domain Fusion Protein (PIF-AD)/-Repressor Domain (PIF-RD)

To form the phytochrome-interacting Factor (PIF)-activation domain fusion protein (PIF-AD) and repressor domain fusion protein (PIF-RD) chimeric gene constructs, DNA fragments may be ligated in accordance with conventional techniques known in the art. Such techniques include use of restriction enzymes to convert sticky-ended fragments to blunt ends (or vice-versa), polymerases and nucleotides to fill in sticky ends to form blunt ends, alkaline phosphatase to avoid undesired ligations, and ligases to join fragments. Phytochrome interacting protein (PIF) is a protein that binds to and/or interacts with phytochrome. An example of such a PIF is described in Ni, et al. Cell 95:657–667; Ni, et al. Nature 400:781–784 and Martinez-Garcia, et al. Science 288:859–863. In this invention, PIF homologs with as low as 40% or more sequence identity to known PIFs find use in the invention so long as they bind to and/or interacts with phytochrome as described herein.

The activation and repressor domain swill generally be cloned from the same cell type as the target gene of interest. However, any activation or repressor domain will suffice so long as it binds to the target gene of interest and activates or represses transcription, as desired.

4. Chromophores

To form the chromophore gene constructs, DNA fragments may be ligated in accordance with conventional techniques known in the art. Such techniques include use of restriction enzymes to convert sticky-ended fragments to blunt ends (or vice-versa), polymerases and nucleotides to fill in sticky ends to form blunt ends, alkaline phosphatase to avoid undesired ligations, and ligases to join fragments. The chromophore gene constructs comprise genes involved in chromophore biosynthesis. Representative genes include, but are not limited to, an *Arabidopsis* ferredoxin-dependent heme oxygenase-encoding gene, designated HY1, (accession numbers: HY1 gene—AB021857; HY1 protein—BAA77758)(Davis et al., 1999; Muramoto et al., 1999), a Synechocystis ferredoxin-dependent heme oxygenase-encoding gene, designated ho1 (accession number: D90901) (Willows et al., 2000), and phytochromobilin synthase/ferredoxin-dependent biliverdin reductase-encoding genes, designated HY2 from *Arabidopsis* (accession number: AB045112)(Kohchi et al., 2001) and other organisms (Frankenberg et al., 2001).

Alternatively, the chromophores themselves may be added directly to the cells. The chromophores may be purified by procedures well known in the art [Scheer (1984) in Techniques in Photomorphogenesis (eds Smith, H. and Holmes, M. G.) pp. 227–256 (Academic Press, New York)].) and supplied to the cells directly.

Expression Vectors

Expression vehicles for expression of the DNA constructs of the invention include plasmids or other vectors. In general, such vectors contain control sequences that allow expression in various types of hosts, including prokaryotes. Suitable expression vectors containing the desired coding and control sequences may be constructed using standard recombinant DNA techniques known in the art, many of which are described in Sambrook et al. (1989), Molecular Cloning: A Laboratory Manual, Second Edition, Cold Spring Harbor Laboratory, Cold Spring Habor, N.Y.

An expression vector as contemplated by the present invention is at least capable of directing the replication of the reporter gene construct and the replication and expression of the DNA binding domain-interacting domain construct. One class of vectors utilizes DNA elements that provide autonomously replicating extrachromosomal plasmids derived from animal viruses (e.g., bovine papilloma virus, polyomavirus, adenovirus, or SV40). A second class of vectors relies upon the integration of the desired gene sequences into the host cell chromosome.

Expression vectors useful in the present invention typically contain an origin of replication, a promoter located 5' to (i.e., upstream of) the DNA sequence to be expressed, and a transcription termination sequence. Suitable origins of replication include, for example, the ColE1, pSC101, SV40 and M13 origins of replication. Suitable termination sequences include, for example, the bovine growth hormone, SV40, lacZ and AcMNPV polyhedral polyadenylation signals. Suitable promoters include, for example, the cytomegalovirus promoter, the lacZ promoter, the gal 10 promoter and the AcMNPV polyhedral promoter. The promoter sequence may also be inducible, to allow modulation of expression (e.g., by the presence or absence of nutrients or other inducers in the growth medium). One example is the lac operon obtained from bacteriophage lambda plac5, which can be induced by IPTG.

The expression vectors may also include other regulatory sequences for optimal expression of the desired product. Such sequences include stability leader sequences, which provide for stability of the expression product; secretory leader sequences, which provide for secretion of the expression product; enhancers, which up regulate the expression of the DNA sequence; and restriction enzyme recognition sequences, which provide sites for cleavage by restriction endonucleases. All of these materials are known in the art and are commercially available. See, for example, Okayama (1983), Mol. Cell. Biol., 3: 280.

A suitable expression vector may also include marker sequences, which allow phenotypic selection of transformed host cells. Such a marker may provide prototrophy to an auxotrophic host, biocide resistance (e.g., antibiotic resistance) and the like. The selectable marker gene can either be directly linked to the DNA gene sequences to be expressed, or introduced into the same cell by co-transfection. Examples of selectable markers include neomycin, ampicillin, hygromycin resistance and the like.

The characteristics of the actual expression vector used must be compatible with the host cell that is to be employed. Suitable commercially available expression vectors into which the DNA sequences of the present invention may be inserted include pSPORT, pBluescriptIISK, the *baculovirus* expression vector pBlueBac, and the prokaryotic expression vector pcDNAII, all of which may be obtained from Invitrogen Corp., San Diego, Calif.

Host Cells

A fusion protein of the invention is expressed in a eukaryotic cell by introducing nucleic acid encoding the fusion protein into a host cell, wherein the nucleic acid is in a form suitable for expression of the fusion protein in the host cell. For example, a recombinant expression vector of the invention, encoding the fusion protein, is introduced into a host cell. Alternatively, nucleic acid encoding the fusion protein which is operatively linked to regulatory sequences (e.g., promoter sequences) but without additional vector sequences can be introduced into a host cell. As used herein, the term "host cell" is intended to include any eukaryotic cell or cell line so long as the cell or cell line is not incompatible with the protein to be expressed, the selection system chosen or the fermentation system employed. Non-limiting examples of mammalian cell lines which can be used include CHO dhfr-cells (Urlaub and Chasin (1980) Proc. Natl. Acad. Sci. USA 77:4216–4220), 293 cells (Graham et al. (1977) J. Gen. Virol. 36: pp 59) or myeloma cells like SP2 or NS0 (Galfre and Milstein (1981) Meth. Enzymol. 73(B) :3–46).

In addition to cell lines, the invention is applicable to normal cells, such as cells to be modified for gene therapy purposes or embryonic cells modified to create a transgenic or homologous recombinant animal. Examples of cell types of particular interest for gene therapy purposes include hematopoietic stem cells, myoblasts, hepatocytes, lymphocytes, neuronal cells and skin epithelium and airway epithelium. Additionally, for transgenic or homologous recombinant animals, embryonic stem cells and fertilized oocytes can be modified to contain nucleic acid encoding a transactivator fusion protein. Moreover, plant cells can be modified to create transgenic plants.

The invention is broadly applicable and encompasses non-mammalian eukaryotic cells as well, including insect (e.g,. Sp. *frugiperda*), yeast (e.g., *S. cerevisiae, S. pombe, P. pastoris, K lactis, H. polymorpha*; as generally reviewed by Fleer, R. (1992) Current Opinion in Biotechnology 3(5) :486–496)), fungal and plant cells. Examples of vectors for expression in yeast *S. cerivisae* include pYepSec1 (Baldari. et al., (1987) Embo J. 6:229–234), pMFa (Kuijan and Herskowitz, (1982) Cell 30:933–943), pJRY88 (Schultz et al., (1987) Gene 54:113–123), and pYES2 (Invitrogen Corporation, San Diego, Calif.). The fusion protein can be expressed in insect cells using baculovirus expression vectors (e.g., as described in O'Reilly et al. (1992) Baculovirus Expression Vectors: A Laboratory Manual, Stockton Press). Baculovirus vectors available for expression of proteins in cultured insect cells (e.g., SF 9 cells) include the pAc series (Smith e al., (1983) Mol. Cell Biol. 3:2156–2165) and the pVL series (Lucklow, V. A., and Summers, M. D., (1989) Virology 170:31–39).

Introduction of Nucleic Acid into a Host Cell

Nucleic acid including those encoding the fusion protein can be introduced into a host cell by standard techniques for transfecting eukaryotic cells. The term "transfecting" or "transfection" is intended to encompass all conventional techniques for introducing nucleic acid into host cells, including calcium phosphate co-precipitation, DEAE-dextran-mediated transfection, lipofection, electroporation and microinjection. Suitable methods for transfecting host cells can be found in Sambrook et al. (Molecular Cloning: A Laboratory Manual, 2nd Edition, Cold Spring Harbor Laboratory press (1989)), and other laboratory textbooks.

The number of host cells transformed with a nucleic acid of the invention will depend, at least in part, upon the type of recombinant expression vector used and the type of transfection technique used. Nucleic acid can be introduced into a host cell transiently, or more typically, for long term regulation of gene expression, the nucleic acid is stably integrated into the genome of the host cell or remains as a stable episome in the host cell. Plasmid vectors introduced into mammalian cells are typically integrated into host cell DNA at only a low frequency. In order to identify these integrants, a gene that contains a selectable marker (e.g., drug resistance) is generally introduced into the host cells along with the nucleic acid of interest. Preferred selectable markers include those which confer resistance to certain drugs, such as G418 and hygromycin. Selectable markers can be introduced on a separate plasmid from the nucleic acid of interest or, are introduced on the same plasmid. Host cells transfected with a nucleic acid of the invention (e.g., a recombinant expression vector) and a gene for a selectable marker can be identified by selecting for cells using the selectable marker. For example, if the selectable marker encodes a gene conferring neomycin resistance, host cells which have taken up nucleic acid can be selected with G418. Cells that have incorporated the selectable marker gene will survive, while the other cells die.

Nucleic acids of the invention can be introduced into eukaryotic cells growing in culture in vitro by conventional transfection techniques (e.g., calcium phosphate precipitation, DEAE-dextran transfection, electroporation etc.). Nucleic acid can also be transferred into cells in vivo, for example by application of a delivery mechanism suitable for introduction of nucleic acid into cells in vivo, such as retroviral vectors (see e.g., Ferry, N et al. (1991) Proc. Natl. Acad. Sci. USA 88:8377–8381; and Kay, M. A. et al. (1992) Human Gene Therapy 3:641–647), adenoviral vectors (see e.g., Rosenfeld, M. A. (1992) Cell 68:143–155; and Herz, J. and Gerard, R. D. (1993) Proc. Natl. Acad. Sci. USA 90:2812–2816), receptor-mediated DNA uptake (see e.g., Wu, G. and Wu, C. H. (1988) J. Biol. Chem. 263:14621; Wilson et al. (1992) J. Biol. Chem. 267:963–967; and U.S. Pat. No. 5,166,320), direct injection of DNA (see e.g., Acsadi et al. (1991) Nature 332:815–818; and Wolff et al. (1990) Science 247:1465–1468) or particle bombardment (see e.g., Cheng, L. et al. (1993) Proc. Natl. Acad. Sci. USA 90:4455–4459; and Zelenin, A. V. et al. (1993) FEBS Letters 315:29–32). Thus, for gene therapy purposes, cells can be modified in vitro and administered to a subject or, alternatively, cells can be directly modified in vivo.

Transgenic Organisms

Nucleic acids encoding the proteins of the invention can be transferred into a fertilized oocyte of a non-human animal to create a transgenic animal which expresses the proteins of the invention in one or more cell types. A transgenic animal is an animal having cells that contain a transgene, wherein the transgene was introduced into the animal or an ancestor of the animal at a prenatal, e.g., an embryonic, stage. A transgene is a DNA which is integrated into the genome of a cell from which a transgenic animal develops and which remains in the genome of the mature animal, thereby directing the expression of an encoded gene product in one or more cell types or tissues of the transgenic animal. In one embodiment, the non-human animal is a mouse, although the invention is not limited thereto. In other embodiments, the transgenic animal is a goat, sheep, pig, cow or other domestic farm animal. Such transgenic animals are useful for large scale production of proteins (so called "gene pharming").

A transgenic animal can be created, for example, by introducing a nucleic acid encoding the fusion protein (typically linked to appropriate regulatory elements, such as a constitutive or tissue-specific enhancer) into the male pronuclei of a fertilized oocyte, e.g., by microinjection, and allowing the oocyte to develop in a pseudopregnant female foster animal. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and Hogan, B. et al., (1986) A Laboratory Manual, Cold Spring Harbor, N.Y., Cold Spring Harbor Laboratory. A transgenic founder animal can be used to breed additional animals carrying the transgene.

It will be appreciated that, in addition to transgenic animals, the regulatory system described herein can be applied to other transgenic organisms, such as transgenic plants. Transgenic plants can be made by conventional techniques known in the art. Accordingly, the invention encompasses non-human transgenic organisms, including animals and plants, that contains cells which express the transactivator fusion protein of the invention (i.e., a nucleic acid encoding the transactivator is incorporated into one or more chromosomes in cells of the transgenic organism).

Homologous Recombinant Organisms

The invention also provides a homologous recombinant non-human organism expressing the proteins of the invention. The term "homologous recombinant organism" as used herein is intended to describe an organism, e.g. animal or plant, containing a gene which has been modified by homologous recombination between the gene and a DNA molecule introduced into a cell of the animal, e.g., an embryonic cell of the animal. In one embodiment, the non-human animal is a mouse, although the invention is not limited thereto. An animal can be created in which nucleic acid encoding the fusion protein has been introduced into a specific site of the genome, i.e., the nucleic acid has homologously recombined with an endogenous gene.

To create such a homologous recombinant animal, a vector is prepared which contains DNA encoding the fusion protein flanked at its 5' and 3' ends by additional nucleic acid of a eukaryotic gene at which homologous recombination is to occur. The additional nucleic acid flanking that encoding the fusion protein is of sufficient length for successful homologous recombination with the eukaryotic gene. Typically, several kilobases of flanking DNA (both at the 5' and 3' ends) are included in the vector (see e.g., Thomas, K. R and Capecchi, M. R. (1987) Cell 51:503 for a description of homologous recombination vectors). The vector is introduced into an embryonic stem cell line (e.g., by electroporation) and cells in which the introduced DNA has homologously recombined with the endogenous DNA are selected (see e.g., Li, E. et al. (1992) Cell 69:915). The selected cells are then injected into a blastocyst of an animal (e.g., a mouse) to form aggregation chimeras (see e.g., Bradley, A. in Teratocarcinomas and Embryonic Stem Cells: A Practical Approach, E. J. Robertson, ed. (IRL, Oxford, 1987) pp. 113–152). A chimeric embryo can then be implanted into a suitable pseudopregnant female foster animal and the embryo brought to term. Progeny harbouring the homologously recombined DNA in their germ cells can be used to breed animals in which all cells of the animal contain the homologously recombined DNA.

In addition to the homologous recombination approaches described above, enzyme-assisted site-specific integration systems are known in the art and can be applied to the components of the regulatory system of the invention to integrate a DNA molecule at a predetermined location in a second target DNA molecule. Examples of such enzyme-assisted integration systems include the Cre recombinase-lox target system (e.g., as described in Baubonis, W. and Sauer, B. (1993) Nucl. Acids Res. 21:2025–2029; and Fukushige, S. and Sauer, B. (1992) Proc. Natl. Acad. Sci. USA 89:7905–7909) and the FLP recombinase-FRT target system (e.g., as described in Dang, D. T. and Perrimon, N. (1992) Dev. Genet. 13:367–375; and Fiering, S. et al. (1993) Proc. Natl. Acad. Sci. USA 90:8469–8473).

Kits

The invention provides kits for detecting interaction between a protein of interest and a sample protein. In an illustrative embodiment, the kit includes at least one construct and a host cell. In a preferred embodiment, the kits may include one or more DNA constructs including: (1) a target gene DNA construct; (2) a DNA construct encoding a phytochrome-DNA-binding-domain fusion protein (PDBP); (3) a DNA construct encoding a phytochrome-interacting factor (PIF)-activation domain fusion protein (PIF-AD) or a DNA construct encoding a phytochrome-interacting factor (PIF)-repressor domain fusion protein (PIF-RD) and (4) a DNA construct encoding chromophore biosynthetic proteins.

The kit may include a suitable light source for use in converting phytochrome from Pr to Pfr and vice versa. Any light that provides red (peak maximum 665 nm) and/or far-red (peak maximum 730–760 nm) wavelengths will suffice. For rapid conversions of phytochrome, high intensity, narrow bandwidth light sources, such as light emitting diodes (LEDs) or lasers will suffice. Alternatively, incandescent or fluorescent lamps of suitable spectral emission, filtered through optical filters of appropriate wavelength, will suffice.

The kit may also include instructions for use. The kit can also include cells into which one can introduce the constructs of the invention, or cells already expressing the phytochrome chromophore, either naturally (plant cells) or driven by introduced transgenes encoding chromophore biosynthesis genes (non-plant cells, such as yeast or animal cells). The cells may include naturally occurring genes to be regulated by the components of the kit. The kit can also include purified chromophore for administration to the cells.

Other Uses for the Methods Described Herein

The methods described herein can be used for a variety of different purposes. The present invention provides instantaneous, non-invasive, reversible induction or repression of target genes, that can be simply and precisely controlled in a temporal and/or spatial fashion. The system is potentially applicable to any host cell or organism, including human. Precisely directed microbeams of light using lasers and/or fiber optics have the potential to activate or repress genes in single cells or small clusters, deep inside multicellular organisms, providing possible therapeutic uses such as in treating human cancers.

The invention will be better understood by reference to the following non-limiting Examples.

EXAMPLES

Example 1

Experimental Protocol

Construction of Yeast Two-Hybrid Vectors. The pGAD424 vector containing the Gal4 activation domain (GAD) was obtained from Clontech (Palo Alto, Calif.), and the D153 vector containing the Gal4 DNA binding domain (GBD) was provided by Dr. Robert M. Brazas (Department of Microbiology, University of California at San Francisco). The full length phyA cDNA was amplified by PCR from a full-length PHYA cDNA using primers containing restriction sites [5'-GGGGATCCAATGTCAGGCTCTAGGCCG-3' (SEQ ID NO:6) and 5'-CCCCCGG GTACTTGTTTGCTGCAGCGAG-3' (SEQ ID NO:7)] and cloned into the BamHI-SmaI sites of D153 creating phyA (FL). The N-terminal domain of phyB (aa 1–621) was amplified by PCR from a full-length PHYB cDNA using primers containing restriction sites [5'-TATAAGAAGAGGCGGCCGCAAATGGTTTCCGGA GTCGGGGGTAG-3' (SEQ ID NO:8) and 5'-TATAAGAAG AGGCGGCCGCAAAGATTCTTTAAAAGAGTCTCT CAG-3' (SEQ ID NO:9)] and cloned into the NotI site of D153 creating phyB (NT). The full length phyB was amplified by PCR from the full-length PHYB cDNA using primers containing restriction sites [5'-TATAAGAAGAGGCGGCCGCAAATGGTTTCCGGA GTCGGGGGTAG-3' (SEQ ID NO:10) and 5'-TATAAGAAGAGGCGGCCGCAAATATGGCATCA TCAGCATC ATG-3' (SEQ ID NO:11)] and cloned into the NotI site of D153 creating phyB (FL). All the constructs were sequenced using an Amersham Pharmacia sequencing kit and a 373 DNA sequencer (Perkin-Elmer). The construction of PIF3:GAD in pGAD424 vector is described by Ni et al.[14].

Yeast Two-Hybrid Plate Assay. The yeast strain AH109 (MATα, ura3–52, his3–200, ade2–101, trp1–901, leu2–3, 112, gal4Δ, met⁻, gal80Δ, URA3::GAL1$_{UAS}$-GAL1$_{TATA}$-lacZ)$_{28}$ was obtained from Clontech. Yeast transformations were performed according to the Clontech Yeast Protocols Handbook (Clontech, Palo Alto). For the phyA (FL) assay, after heat-treatment, the yeast were spread on non-selective synthetic dropout (SD) media SD(-LW), and incubated for 2 days. The colonies were scraped, and re-suspended in buffered glycerol solution (32.5% glycerol, 50 mM MgSO$_4$, 12.5 mM Tris-HCl [pH 8.0]). The glycerol solution was spread on SD(-LWHA) containing 1 mM 3-aminotriazole (3-AT) with or without 25 μM PCB, and incubated under continuous red light (Rc) (1 μmol m$^{-2}$s$^{-1}$) or in the darkness for 3 days. For the phyB(NT) assay, after heat-treatment, the yeast cells were cultured in SD(-LWH) media with or without 25 μM PCB in darkness for 3 hr. The transformants were spread on SD(-LWHA) with or without 25 μM PCB, and incubated under Rc (1 μmol m$^{-2}$s$^{-1}$) or in the darkness for 3 days. PCB was purified from Spirulina according to Scheer et al.[29].

Yeast Two-Hybrid Quantitative Liquid Assay

The yeast strain Y187 (MATa, ura3–52, his3–200, trp1–901, leu2–3, 112, gal4Δ, met⁻, gal80Δ, LYS2::GAL1$_{UAS}$-GAL1$_{TATA}$-HIS3, GAL2$_{UAS}$-GAL2$_{TATA}$-ADE2, ura3::MEL1$_{UAS}$-MEL1$_{TATA}$-lacZ)[30] was obtained from Clontech (Palo Alto). Transformants were grown in SD(-LW) media with or without 25 μM PCB under Rc (40 μmol m$^{-2}$s$^{-1}$) or in darkness for 16 hr. The culture was inoculated into YPD media with or without 25 μM PCB under Rc (40 μmol m$^{-2}$s$^{-1}$) or in darkness. The assay of LacZ activity with o-nitrophenyl β-D-galactopyranoside (ONPG, Sigma) as a substrate was performed according to the Clontech Yeast Protocols Handbook.

Light Sources. Red light ($\lambda_{max}$, 660 nm) for longer term irradiations (FIGS. 2, and 3A,B) was provided by filtered fluorescent tubes as described by Parks and Quail[31]. Red light ($\lambda_{max}$, 664 nm) and far-red light ($\lambda_{max}$, 748 nm) used for pulse irradiations (FIGS. 3C,D,E) was provided by light-emitting diode arrays as described by Zhu et al.[9]. All light-sensitive manipulations were performed in darkroom space under green safelight ($\lambda_{max}$, 550 nm) as described by Bolton & Quail[32]. This safelight is absorbed poorly by the phy molecule, and therefore does not significantly activate or deactivate the photoreceptor, whereas green light is sensitively perceived by the human visual system, thereby providing a well-illuminated working environment.

Results and Discussion

Regulatable transgene systems providing easily controlled, conditional induction or repression of expression are indispensable tools in biomedical and agricultural research and biotechnology. Several such systems have been developed for eukaryotes[1-7]. The majority of these rely on the administration of either exogenous chemicals or heat shock. Despite the general success of many of these systems, the potential for problems, such as toxic, unintended or pleiotropic effects of the inducing chemical or treatment, can impose limitations on their use. We have developed a novel promoter system that can be induced, rapidly and reversibly, by short pulses of light. This system is based on the known red-light-induced binding of the plant photoreceptor, phytochrome, to the protein, PIF3, and the reversal of this binding by far-red light[8,9]. We show that yeast cells expressing two chimeric proteins, a GAL4-DNA-binding-domain-phytochrome fusion, and a GAL4-activation-domain-PIF3 fusion, are induced by red light to express selectable or scorable marker genes containing promoters with a GAL4-DNA-binding site, and that this induction is rapidly abrogated by subsequent far-red light. We show further that the extent of induction can be precisely controlled by titrating the number of photons delivered to the cells by the light pulse. This system thus has the potential to provide rapid, noninvasive, switchable control of the expression of any desired gene to a selectable level in any suitable cell by simple exposure to a light signal.

The phytochromes are a family of sensory photoreceptors (designated phyA through phyE in *Arabidopsis*) that regulate plant growth and development in response to informational light signals[10,11]. These molecules are chromoproteins consisting of a polypeptide and a covalently-linked tetrapyrrole chromophore. The polypeptide folds into two major structural domains: the photoactive N-terminal domain that contains the chromophore, and the C-terminal domain that mediates dimerization[12]. The holoprotein has two forms which are reversibly interconvertible by light: the biologically inactive Pr form that absorbs red light, and the biologically active Pfr form that absorbs far-red light[10,11]. When the Pr form absorbs a photon, it is converted to the Pfr form, and when the Pfr form absorbs a photon, it is converted back to the Pr form. This photointerconversion process is complete within milliseconds for any given molecule and is indefinitely repeatable. The molecule is synthesized in the Pr form. Thus, for cells maintained in darkness, the photoreceptor is accumulated in this inactive form, poised for activation by conversion to the Pfr form upon exposure to light.

PIF3, a basic helix-loop-helix (bHLH) protein, has been shown to interact selectively with the Pfr form of both phyA and phyB in vitro upon light activation[8,9,13,14]. We have exploited this light-dependent, conformer-specific interaction to develop a light-switchable gene expression system. The general design of this system, which is based on the yeast two-hybrid concept[15,16], is described in FIG. 1C.

Figure 1C:
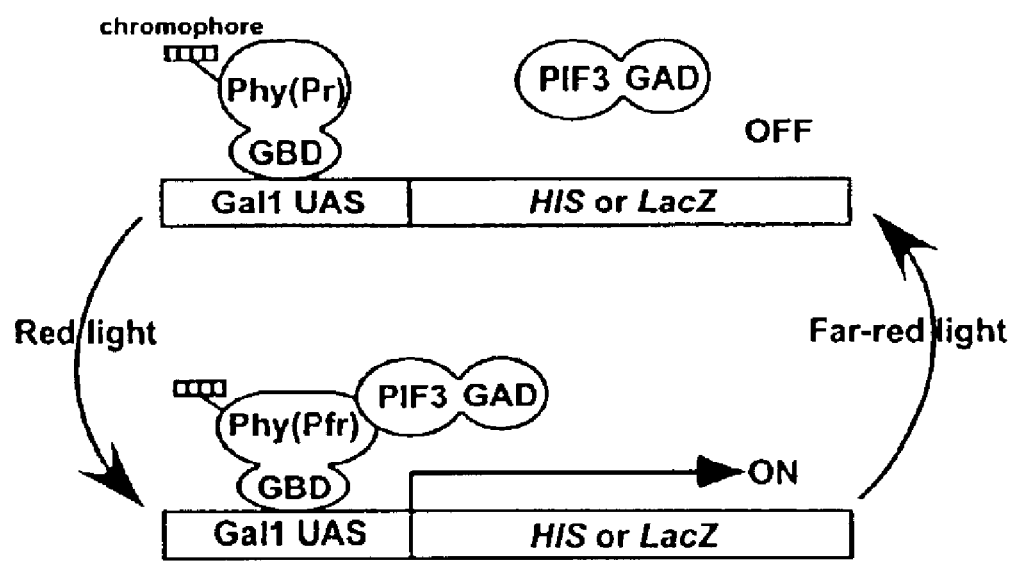
FIG. 1C shows a schematic representation of an exemplary light-switchable gene promoter system.

FIG. 1C shows an exemplary schematic representation of the light-switchable gene promoter system. In this system, cells transformed with the vectors indicated are maintained in darkness until it is desired to activate the expression of the target gene. In darkness, the phy(Pr)-GBD fusion protein is synthesized, and the chromophore is attached to the phytochrome moiety to generate the biologically inactive Pr conformer. This fusion protein will bind to its DNA-binding site in the target gene promoter, via its Gal4 DNA-binding domain, but because the phytochrome moiety is in the Pr conformer, it will not bind to the PIF3-AD protein. In this configuration, the target gene is off. To activate expression of the target gene, cells are exposed to red light. This light wavelength converts the phytochrome moiety within one second to the biologically active Pfr conformer of the photoreceptor that binds the PIF3 moiety of the PIF3-AD fusion protein with high affinity. The photoactivated phy (Pfr)-GBD molecule thereby recruits the PIF3-AD protein to the target promoter where the transcriptional activation domain of PIF3-AD induces transcription of the target gene. To switch off expression of this gene, cells are exposed to far-red light. This wavelength of light switches the phytochrome molecule back to the inactive Pr conformer within one second causing rapid dissociation of PIF3-AD and termination of the transcriptional activation of the target gene. This overall activation-deactivation process can be repeated at will using sequential exposure of cells to red and far-red light. This system can theoretically function in any cell or organism that can either synthesize the chromophore (PCB) endogenously or take up exogenously supplied PCB. A cell or organism can also be genetically engineered to synthesize PCB and assemble holophytochrome as shown in bacteria[24].

To determine whether yeast cells cultured with exogenously-supplied chromophore would synthesize and assemble photoactive phytochrome molecules capable of conformer-specific interaction with PIF3 in vivo, we initially examined phyA and phyB constructs under both selectable and scorable two-hybrid assay conditions. FIG. 2A shows that both full-length phyA and the photosensory N-terminal domain of phyB, each fused to the GAL4-DNA-binding domain (phyA(FL)–GBD and phyB(NT)–GBD, respectively), supported yeast colony growth exclusively in red light on selection medium containing the chromophore, phycocyanobilin (PCB), when cotransformed with the PIF3-GAL4-activation-domain fusion (PIF3-GAD). Red light was ineffective in the absence of exogenous chromophore, and the chromophore was ineffective in darkness. In addition to providing an initial proof of concept, these data establish that the system can be used in a conventional yeast two-hybrid configuration to screen for potential signaling partners that interact specifically with the biologically active Pfr form of the photoreceptors.

Figure 2:
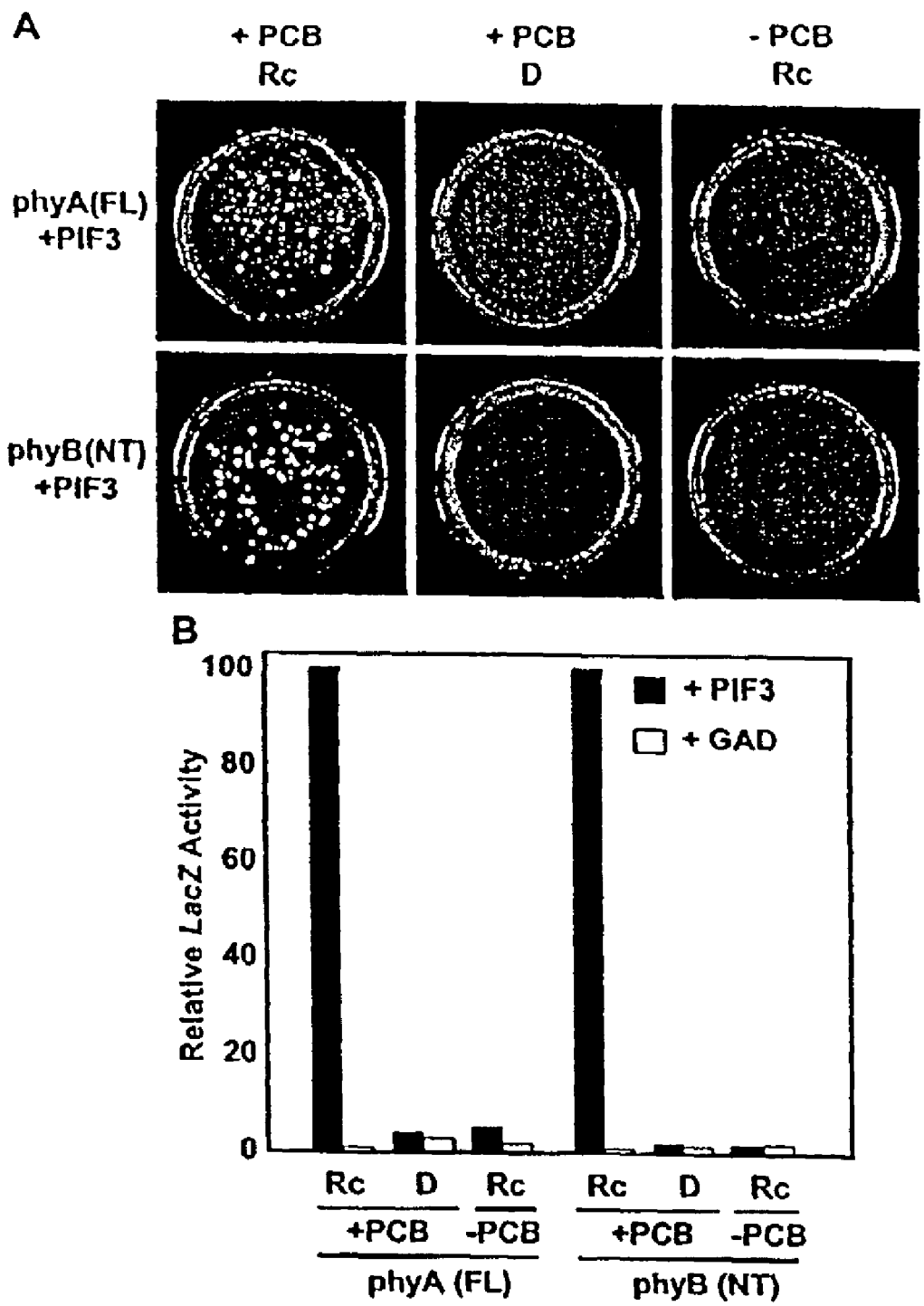
FIG. 2 shows that photoactive phy A and phy B recombinant proteins interact specifically in the Pfr form with PIF3 in living yeast cells.

FIG. 2 shows photoactive phyA and phyB recombinant proteins interact specifically in the Pfr form with PIF3 in living yeast cells. (A) Yeast two-hybrid plate-growth assay. Yeast cells (AH109) were transformed with plasmids encoding a full-length phyA (phyA (FL)):Gal4-DNA-binding-domain (GBD) fusion-protein and a PIF3:Gal4-activation-domain (GAD) fusion-protein [phyA(FL)+PIF3], or phyB N-terminal domain [phyB(NT)]:GBD fusion-protein and the PIF3:GAD fusion-protein [phyB(NT)+PIF3]. The transformants were cultured on selective media in the presence (+) or absence (−) of 25 $\mu$M PCB under continuous red light (Rc) or in the darkness (D) for 3 days. The yeast cells only grew on the selective media containing PCB under Rc. (B) Quantitative yeast two-hybrid liquid assay. Yeast cells (Y187) were transformed with the constructs indicated and cultured in the presence (+) or absence (−) of 25 $\mu$M PCB under Rc or in the darkness (D). LacZ activity was determined and expressed in relative units. Black bars show the relative LacZ activities for phy:GBD with PIF3:GAD, and white bars show the relative LacZ activities for phy:GBD with GAD only. GBD-phytochromes and GAD-PIF3 showed strong induction of LacZ activities in the presence of PCB in Rc.

These results were confirmed and quantitated under non-selective, liquid-culture assay conditions (FIG. 2B). Yeast cells expressing PIF3-GAD and either phyA(FL)–GBD or phyB(NT)–GBD exhibited strong activation of LacZ-marker expression in red light in a PCB-dependent fashion relative to the GAD control under these conditions. The full-length phyB fusion protein (phyB(FL)–GBD) also displayed a red-light- and PCB-dependent activation, but this construct had higher constitutive activity levels than the others thereby reducing its utility for this purpose (data not shown). These results are consistent with previous observations that the isolated, chromophore-conjugated N-terminal domain of phyB exhibits strong, Pfr-specific binding to PIF3 in vitro in addition to the full length photoreceptors[8, 9]. Based on these data, we selected the phyB(NT)–GBD/PIF3-GAD combination of constructs to optimize the light-switchable gene-expression system.

To maximize inducible expression, it is desirable to have maximal levels of the fully assembled photoreceptor-fusion protein in the cell poised to respond to the onset of the light signal. This requires synthesis of the protein, import of the chromophore and assembly of the photoactive chimeric molecule. We therefore examined the effects of a variety of preincubation conditions on the extent of photoinducibility.

Figure 3:
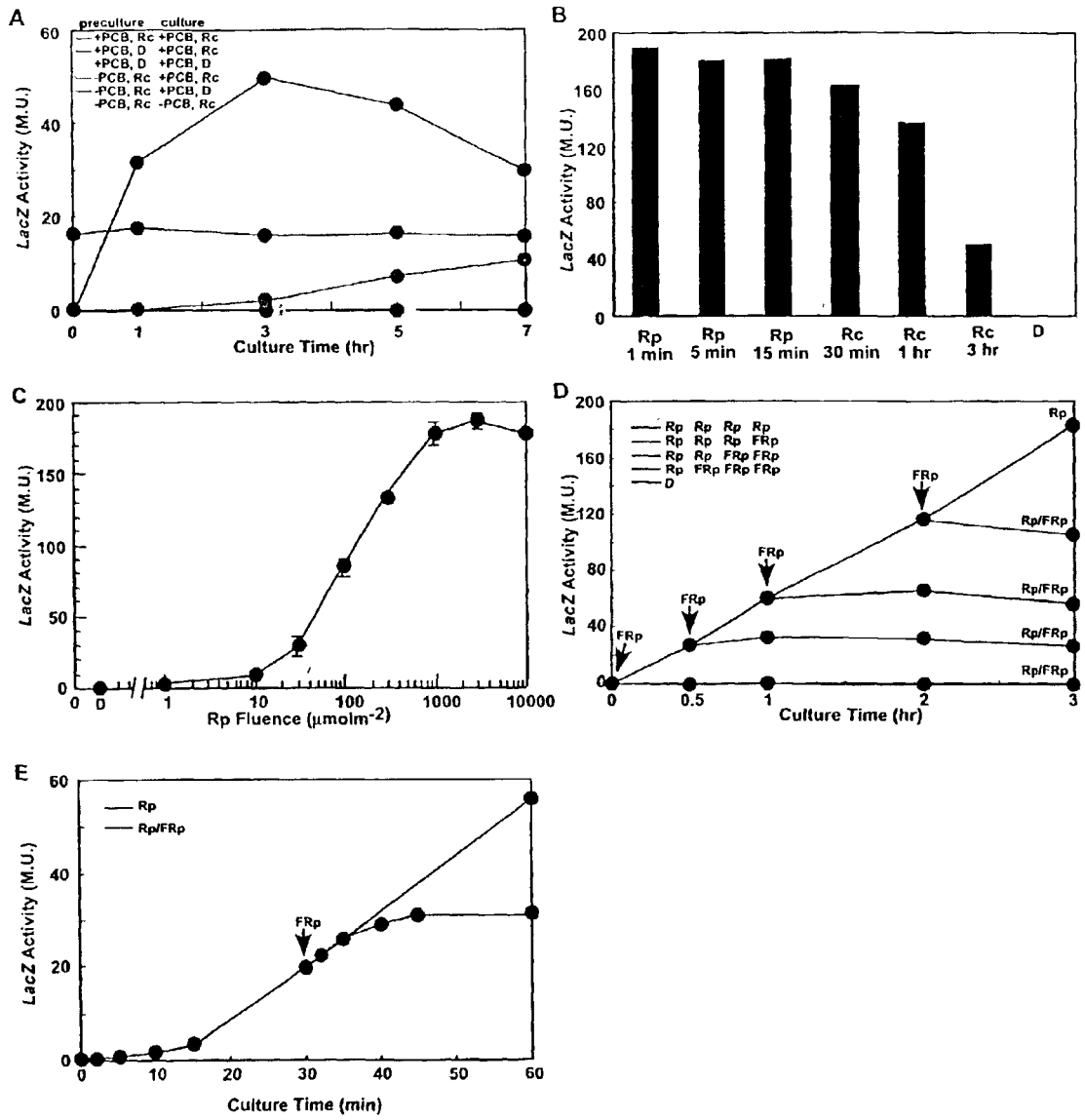
FIG. 3 shows the photoreversible activation of reporter gene expression.

FIG. 3 shows the photoreversible activation of reporter gene expression. (A) Time-course of reporter-gene expression in yeast cells after various preincubation treatments. Yeast cells (Y187) containing phyB(NT):GBD and PIF3:GAD were preincubated under the conditions indicated [with (+) or without (−) 25$\mu$M PCB, and either in Rc or darkness (D)] for 16 hr. These cells were then inoculated into YPD media, and cultured further under the conditions indicated. After 0, 1, 3, 5, and 7 hr, the cells were collected and LacZ activity was determined. Maximum expression is induced by preincubating the cells in the presence of PCB in the dark, and subsequently transferring them to Rc+PCB conditions. (B) Effect of duration of red light irradiation. Yeast cells cotransformed with phyB(NT):GBD and PIF3:GAD were preincubated with PCB in darkness. After inoculation into YPD media, the cultures were given red light pulses (Rp) for the duration indicated and returned to darkness, or were retained in continuous red light (Rc). After 3 hr, LacZ activity was measured. Irradiation of 1 min is sufficient to reach the maximum induction of reporter gene expression. (C) Fluence(dose)-response curve of reporter gene expression in yeast. This experiment was performed as described in FIG. 3B with the exception that a single, short pulse of R-light of varying intensity or duration was given at the start of the 3h culture. (D) Effect of a far-red light pulse (FRp) in reversing red light pulse-induction (Rp) of gene expression. Yeast cells cotransformed with phyB(NT):GBD and PIF3:GAD were preincubated in the presence of PCB in darkness. After inoculation into YPD media, the cultures were given either a 5 min Rp (12,000 $\mu$mol m$^{-2}$), or a 5 min Rp followed by a 5 min FRp (18,600 $\mu$mol m$^{-2}$) at the times indicated (0, 0.5, 1, 2 h after inoculation). (E) short-term kinetics of induction, and reversal of induction of gene expression by Rp and FRp light-pulses. Yeast cells were cotransformed and preincubated as in (D). After inoculation into YPD media, the cultures were given a 1 min Rp (2,400 $\mu$mol m$^{31\ 2}$) and either incubated further in darkness for the periods indicated (Rp), or incubated in darkness for 30 min before being given a 5 min FRp (18,600 $\mu$mol m$^{-2}$) and incubated further in darkness for the periods indicated (Rp/FRp). Yeast cells showed Rp-dependent induction of reporter gene expression which can be turned off rapidly by a subsequent FRp.

FIG. 3A shows that cells preincubated with the chromophore in darkness, plus subsequently during irradiation, exhibited the highest levels of LacZ induction, peaking at 3 hours. By contrast, cells provided with chromophore for the first time at the onset of the light exposure displayed a long lag and relatively weak induction over the irradiation period. These data indicate that chromophore uptake and/or holoprotein assembly is rate-limiting when supplied coincident with the onset of the light signal, and verify the advantage of permitting active photoreceptor assembly prior to exposure. Cells that were preincubated both with PCB and in red light, were already moderately induced at the beginning of the experimental period, but showed no further increase (FIG. 3A). Cells incubated in darkness or without chromophore showed no detectable LacZ activity above background. Based on these experiments, we adopted dark-preincubation in PCB as the standard procedure.

The decline in activity after 3 hours in the plus-PCB, dark-preincubated sample (FIG. 3A), and a visible decline in chromophore color intensity in the media, suggested that chromophore bleaching was occurring in prolonged red-light irradiations. This suggestion is verified by the data in FIG. 3B. These results show that inducibility is maximized by a pulse of red light of only one minute followed by further incubation in the dark (note differences in scale between FIGS. 3A and 3B). Continuous light of 30 minutes or more caused declining activity, with a strong reduction after 3 hours of red light. These data indicate that a single short pulse of light that maximizes conversion of all pre-existing phyB molecules to the active Pfr form at the start of the culture period provides maximal induction during the subsequent dark period. Longer irradiations are not only unnecessary, but potentially deleterious, possibly due to photodynamic damage induced by excess free chromophore.

The photochemical properties of the phytochrome molecule make it possible to accurately control the number of molecules converted to the Pfr form by controlling the number of red photons delivered in a pulse irradiation. FIG. 3C shows the fluence(dose)-response curve for LacZ induction in the transformed yeast by a single red-light pulse. This curve very closely follows well-established data for the phytochromes$_{17,18}$ and is indicative of the photochemical and functional integrity of the photoreceptor in the yeast cells. The data demonstrate that this system can be used to provide a precisely regulated and reproducible level of expression of the target gene by delivering a readily pre-defined number of photons to the cells in a single, short light pulse at the start of the culture period.

The unique photoreversibility of the phytochrome system makes it possible to use the photoreceptor as a molecular switch. We showed previously that the red-light-induced binding of phyB to PIF3 in vitro is rapidly reversed by subsequent far-red light[8,13] (FIG. 1). To determine whether this property could be used to reverse the induction of LacZ activity in our system in vivo, pulse-red-light-induced yeast cells were subsequently exposed to pulses of far-red light, either immediately (time zero), or at 0.5, 1 or 2 hours after the start of the culture period (FIG. 3D). The data show that the far-red pulse blocks any further apparent increase in LacZ activity beyond that reached at the time of this pulse. It appears, therefore, that reconversion of the Pfr form to the Pr form in the yeast cell effectively terminates the red-light induced expression, presumably by dissociation of PIF3-GAD from the photoreceptor.

To determine more accurately how rapidly expression can be induced and repressed in our system, we performed a more detailed short-term time-course analysis (FIG. 3E). The data show that LacZ activity is induced 2-fold by 5 min, 4-fold by 10 min and 50-fold by 30 min after a 1 min saturating red-light pulse. Conversely, a decrease in the rate of LacZ accumulation is detectable within 10 min of a far-red-light pulse given to fully induced cells 30 min after the initial red pulse. Cessation of further LacZ accumulation is complete by 15 min after the far-red pulse. The speed of red-light triggered induction of LacZ accumulation appears to be comparable to, or more rapid than, that reported for galactose induction in yeast[19, 20, 21]. The brief lag in detectable LacZ accumulation after the red light pulse may reflect the inherent time required for transcription and translation after transcriptional initiation in yeast cells[19]. Similarly, the short lag before observable cessation of LacZ accumulation after the far-red pulse could reflect the inherent period for turnover of residual translatable LacZ transcript in the cell, or establishment of steady-state equilibrium rates of LacZ protein synthesis and degradation driven by the finite mRNA pool produced during the 30 min induction period[22].

Table 1 shows the absolute levels of expression provided by our optimized assay system compared to that of the native GAL4 protein under the same conditions. The data show that the expression level for the phyB/PIF3 pair in darkness is indistinguishable from the background level of the GBD/GAD negative control. A single red-light pulse induces expression 1000-fold or more above background, and a subsequent far-red pulse completely blocks induction above this background level. In absolute terms, the level of red-light induced expression is about one-sixth of that of the native GAL4 protein under these conditions (Table 1). Taken together, these data show that, although the absolute expression level of the light-inducible two-component system is not as high as that of the intact, parent GAL4 activator, expression is nevertheless inducible over a large dynamic range above a background level that is negligible in the absence of the inducer, and that induction is fully abrogated by switching off the activated state of the phyB molecule.

Various authors have outlined the features of the ideal regulatable gene expression system[4-6]. These include negligible basal expression in the absence of the inducer; rapid, reversible, dose-dependent, high-level, gene-specific induction of expression upon administration of the inducer; and use of an inducer that is inexpensive, non-toxic, accurately dosable, lacking pleiotropic and unintended effects, simple to administer, and combinable with cell or tissue specific expression. The light-switchable system described here has most, if not all, of these features. Basal levels of expression are low, but rapidly and reversibly induced to high levels by the light signal (FIG. 3; Table 1). Since the interacting factors are poised in the nucleus and red-light-induced Pr to Pfr conversion occurs within milliseconds, transcriptional induction can potentially initiate within seconds. Reversal of induction may be similarly rapid, requiring only dissociation of PIF3 from phyB after farred-light induced Pfr to Pr conversions[8]. This property permits highly synchronous and uniform induction of expression across cell populations. The level of expression is precisely controlled (FIG. 3C). This is because the extent of photoconversion of Pr to Pfr is directly proportional to the number of red photons delivered to the system in a highly predictable and reproducible manner[17, 18]. In addition to providing this precise dose-control, light is an inexpensive, universally available, simple-to-use, non-toxic inducer that is readily usable with many systems. Any cells to which light can be delivered are potential targets, including single-celled organisms, cultured cells, and light-penetrant multicellular organisms, such as worms, flies and plants. Directed light delivery via fiber optics has the potential to target selected tissues or cell types, even within larger, more opaque organisms, thus providing the opportunity to investigate the consequences of cell-specific expression and for possible therapeutic applications. Although the present configuration of the light-switchable system provides inducible gene expression, the polarity can potentially be reversed to provide reversible light-imposed repression of expression, by configuring the interacting phy and PIF3 partners to repress the activity of a constitutively active promoter. It is anticipated that exogenously supplied chromophore, as used here, will be readily absorbed by other cell systems, including those of multicellular organisms, such as flies and worms, based on the demonstration that *Arabidopsis* mutants null for chromophore biosynthesis are fully rescued by PCB exogenously supplied to whole, living seedlings[23]. Alternatively, it is possible to engineer cells to produce their own chromophore, as reported recently for bacteria[24], or, in the case of plants, to exploit the naturally-produced, endogenous chromophore[25-27].

Based on the above considerations, we conclude that the system described here has the potential to provide exquisitely precise, quantitative, spatiotemporal control of conditional expression of selected genes in any light-accessible eukaryotic cell using a universally available, non-invasive, non-toxic inducer.

TABLE 1

Basal and light-inducible expression levels compared to native GAL4 activation[a]

| Introduced constructs[b] | LacZ activity (M. U.)[c] | | |
|---|---|---|---|
| | Dark | Rp | Rp/FRp |
| GBD + GAD | 0.1 ± 0.03 | 0.2 ± 0.03 | 0.2 ± 0.05 |
| phyB(NT):GBD + GAD | 0.2 ± 0.05 | 0.1 ± 0.04 | 0.1 ± 0.03 |
| phyB(NT):GBD + PIF3:GAD | 0.1 ± 0.03 | 191 ± 2 | 0.1 ± 0.03 |
| GBD:GAD (native GAL4 protein) | 1146 ± 9 | 1127 ± 10 | 1138 ± 5 |

[a]Yeast cells transformed with the constructs indicated were cultured and assayed as in FIG. 3C. Transformed cells were either kept in the dark, exposed to a single red-light pulse (12 × 10$^3$ µmol m$^{-2}$) and returned to darkness for 3 h (Rp), or exposed to the Rp followed immediately by a far-red-light pulse (18.6 × 10$^3$ µmol m$^{-2}$) and returned to darkness for 3 h (Rp/FRp), and then assayed for LacZ reporter activity.
[b]Cells were co-transformed with plasmids expressing the indicated proteins: GBD, GAL4 DNA-binding domain; GAD, GAL4-activation domain; phyB(NT):GBD, phyB(NT)-GBD fusion protein; PIF3:GAD, PIF3-GAD fusion protein; GBD:GAD, native GAL4 protein.
[c]LacZ assays were performed in triplicate and the values represent the means ± standard error.

Example 2

Purification of Phycocyanobilin (PCB) Chromophore

Fifty grams of *Spirulina* (Sigma S-9134) was suspended in 1.5 liters water and the insoluble materials removed by centrifugation (8000 rpm, 40C, 1 h). Trichloroacetic acid was added to the supernatant to a final concentration of 1.5% (w/v) and stirred at 40C for 1 h in the dark. The precipitate was collected by centrifugation (8000 rpm, 40C, 10 min), resuspended using a tissue homogenizer and washed with 1.5 liters methanol. This process was repeated four times. The final, washed pellet was resuspended in 500 ml methanol. All subsequent steps were performed in the dark. Methanolysis was performed by heating the suspension to 750C for approximately 8 h. The volume was reduced to 50 ml by vacuum and 100 ml water was added. Phycocyanobilin (PCB) was extracted by the addition of 50 ml chloroform and collected using a separatory funnel. The solution was then dried under nitrogen gas, and the PCB dissolved in 2 ml dimethylsulfoxide (DMSO). (or, simply: Scheer, H. in Techniques in Photomorphogenesis (Eds Smith, H. & Holmes, M. G.) 227–256 (Academic, London, N.Y., 1984).) The following references are hereby incorporated by reference in their entirety.

REFERENCES

1. Blau, H. M. & Rossi, F. M. V. Tet B or not tet B: Advances in tetracycline-inducible gene expression. *Proc. Natl. Acad. Sci. USA* 96, 797–799 (1999).
2. Caddick, M. X., Greenland, A. J., Jepson, I., Krause, K. P., Qu, N., Riddell, K. V., Salter, M. G., Schuch, W., Sonnewald, U. & Tomsett, A. B. An ethanol inducible gene switch for plants used to manipulate carbon metabolism. *Nature Biotech.* 16, 177–180 (1998).
3. Gatz, C. Chemically inducible promoters in transgenic plants. *Curr. Opin. Biotech.* 7, 168–172 (1996).
4. Gatz, C. Chemical control of gene expression. *Annu. Rev. Plant Physiol. Plant Mol. Biol.* 48, 89–108 (1997).
5. Lewandoski, M. Conditional control of gene expression in the mouse. *Nature Rev. Genetics* 2, 743–755 (2001).
6. Mills, A. A. Changing colors in mice: an inducible system that delivers. *Genes & Dev.* 15, 1461–1467 (2001).
7. Roslan, H. A., Salter, M. G., Wood, C. D., White, M. R. H., Croft, K. P., Robson, F., Coupland, G., Doonan, J., Laufs, P., Tomsett, A. B. & Caddick, M. X. Characterization of the ethanol-inducible alc gene-expression system in *Arabidopsis thaliana*. *Plant J.* 28, 225–235 (2001).
8. Ni, M., Tepperman, J. M., & Quail, P. H. Binding of phytochrome B to its nuclear signaling partner PIF3 is reversibly induced by light. *Nature* 400, 781–784 (1999).
9. Zhu, Y., Tepperman, J. M., Fairchild, C. D., & Quail, P. H. Phytochrome B binds with greater apparent affinity than phytochrome A to the basic helix-loop-helix factor PIF3 in a reaction requiring the PAS domain of PIF3. *Proc. Natl. Acad. Sci. USA* 97, 13419–13424 (2000).
10. Quail, P. H. Phytochrome photosensory signalling networks. *Nature Rev./Mol. Cell Biol.* 3, 85–93 (2002).
11. Smith, H. Phytochromes and light signal perception by plants—An emerging synthesis. *Nature* 407, 585–591 (2000).
12. Quail, P. H. An emerging molecular map of the phytochromes. *Plant Cell Environ.* 20, 657–665 (1997).
13. Martínez-García, J. F., Huq, E. & Quail, P. H. Direct targeting of light signals to a promoter element-bound transcription factor. *Science* 288, 859–863 (2000).
14. Ni, M., Tepperman, J. M., and Quail, P. H. PIF3, a phytochrome-interacting factor necessary for normal photoinduced signal transduction, is a novel basic helix-loop-helix protein. *Cell* 95, 657–667 (1998).
15. Brent, R. & Finley Jr., R. L. Understanding gene and allele function with two-hybrid methods. *Annu. Rev. Genet.* 31, 663–704 (1997).
16. Phizicky, E. M. & Fields, S. Protein-protein interactions: Methods for detection and analysis. *Microbiol. Rev.* 59, 94–123 (1995).
17. Colbert, J. T., Hershey, H. P. & Quail, P. H. Autoregulatory control of translatable phytochrome mRNA levels. *Proc. Natl. Acad. Sci. USA* 80, 2248–2252 (1983).
18. Smith, H. & Jackson, G. M. Rapid phytochrome regulation of wheat seedling extension. *Plant Physiol.* 84, 1059–1062 (1987).
19. St. John, T. P. & Davis, R. W. The organization and transcription of the galactose gene cluster of *Saccharomyces*. *J. Mol. Biol.* 152, 285–315 (1981).
20. Abe, A., Wada, T., Handa, H., Nogi, Y. & Fukasawa, T. Efficient usage of a galactose-inducible expression vector for the production of heterologous protein in yeast. *Agric. Biol. Chem.* 52, 2035–2041 (1988).
21. Ronicke, V., Graulich, W., Mumberg, D., Muller, R. & Funk, M. Use of conditional promoters for expression of heterologous proteins in *Saccharomyces cerevisiae*. *Meth. Enzym.* 283, 313–322 (1997).
22. Parker, R., Herrick, D., Peltz, S. W. & Jacobson, A. Measurement of mRNA decay rates in *Saccharomyces cerevisiae*. *Meth. Enzym.* 194, 415–423 (1991).
23. Parks, B. M. & Quail, P. H. Phytochrome-Deficient hy1 and hy2 Long Hypocotyl Mutants of *Arabidopsis* Are Defective in Phytochrome Chromophore Biosynthesis. *Plant Cell* 3, 1177–1186 (1991).
24. Gambetta, G. A. & Lagarias, J. C. Genetic engineering of phytochrome biosynthesis in bactera. *Proc. Natl. Acad. Sci. USA* 98, 10566–10571 (2001).
25. Boylan, M. T. & Quail, P. H. Phytochrome A overexpression inhibits hypocotyl elongation in transgenic *Arabidopsis*. *Proc. Natl. Acad. Sci. USA* 88, 10806–10810 (1991).
26. Boylan, M., Douglas, N. & Quail, P. H. Dominant negative suppression of *Arabidopsis* photoresponses by mutant phytochrome A sequences identifies spatially discrete regulatoy domains in the photoreceptor. *Plant Cell* 6, 449–460 (1994).
27. Wagner, D., Tepperman, J. M. & Quail, P. H. Overexpression of phytochrome B induces a short hypocotyl phenotype in transgenic *Arabidopsis*. *Plant Cell* 3, 1275–1288 (1991).
28. Harper, J. W., Adami, G. R., Wei, N., Keyomarsi, K. & Elledge, S. J. The p21 Cdk-interacting protein Cip1 is a potent inhibitor of G1 cyclin-dependent kinases. *Cell* 75, 805–816 (1993).
29. Scheer, H. Model compounds for the phytochrome chromophore. in *Techniques in Photomorphogenesis*. (eds Smith, H. & Holmes, M. G.) 227–256 (Academic Press, New York, 1984).
30. James, P., Halliaday, J. & Craig, E. A. Genomic libraries and a host strain designed for highly efficient two-hybrid selection in yeast. *Genetics* 144, 1425–1436 (1996).
31. Parks, B. M. & Quail, P. H. hy8, a new class of *Arabidopsis* long hypocotyl mutants deficient in functional phytochrome A. *Plant Cell* 5, 39–48 (1993).
32. Bolton, G. W. & Quail, P. H. Cell-free synthesis of phytochrome apoprotein. *Planta* 155, 212–217 (1982).
33. Quail, P. H. Photosensory perception and signaling in plant cells: new paradigms? *Current Opinion in Cell Biol.* 14:180–188 (2002).

We claim:

1. A cell, comprising:
   a target gene;
   a first recombinant fusion protein including a phytochrome and a DNA binding protein and
   a second recombinant fusion protein including a phytochrome interacting protein and a transcriptional regulatory protein.

2. The cell of claim 1 wherein the target gene is a recombinant target gene.

3. The cell of claim 1 wherein the target gene is a gene naturally occurring within said cell.

4. The cell of claim 1 further comprising one or more recombinant chromophore biosynthetic proteins.

5. The cell of claim 1 wherein said transcriptional regulatory protein is a repressor domain or an activator domain.

6. The cell of claim 1 further comprising an exogenously supplied chromophore.

7. The cell of claim 1 wherein said cell is selected from the group consisting of plant, algae, fungi, yeast and animal cells.

8. The cell of claim 7 wherein said animal cell is selected from the group consisting of mammalian, insect, worm, and fish cells.

9. The cell of claim 8 wherein said mammalian cell is an isolated human cell.

10. The cell of claim 1 wherein said transcriptional regulatory protein is an activator.

11. The cell of claim 1 wherein said transcriptional regulatory protein is a repressor.

12. A cell, comprising:
    a target gene;
    a first recombinant DNA construct encoding a fusion protein including a phytochrome and a DNA binding protein and
    a second recombinant DNA construct encoding a fusion protein including a phytochrome interacting protein and a transcriptional regulatory protein.

13. The cell of claim 12 wherein said target gene is a recombinant target gene.

14. The cell of claim 12 wherein the target gene is a gene naturally occurring within said cell.

15. The cell of claim 12 wherein said first and said second DNA constructs further include a promoter active in said cell.

16. The cell of claim 12 further comprising a third DNA construct encoding a chromophore biosynthetic protein.

17. A kit, comprising:
    a first DNA construct encoding a fusion protein including a phytochrome and a DNA binding protein and
    a second DNA construct encoding a fusion protein including a phytochrome interacting protein and a transcriptional regulatory protein.

18. The kit of claim 17 wherein said DNA constructs are cloned into one or more vectors.

19. The kit of claim 17 further including a third DNA construct encoding a target gene.

20. The kit of claim 17 further including instructions for use.

21. The kit of claim 17 further including a light source.

22. The kit of claim 17 further including a chromophore.

23. The kit of claim 17 further including a DNA construct encoding a chromophore biosynthetic protein.

24. The kit of claim 17 wherein said transcriptional regulatory protein is an activator.

25. The kit of claim 17 wherein said transcriptional regulatory protein is a repressor.

26. A method of regulating the expression of a target gene by light, comprising:
    a) incubating a cell, said cell comprising:
       i) said target gene wherein said target gene has a promoter;
       ii) a phytochrome chromophore;
       iii) a first recombinant fusion protein including a phytochrome with Pr and Pfr conformers and a DNA binding protein that binds to said promoter; and
       iv) a second recombinant fusion protein including a phytochrome interacting protein and a transcriptional regulatory protein in the dark, under conditions so that the phytochrome chromophore attaches to the phytochrome to generate said Pr conformer and the DNA binding protein binds to its DNA binding site in said promoter, and b) exposing said cell to sufficient light to convert the Pr conformer to the Pfr conformer to thereby permit the phytochrome to bind to the phytochrome interacting protein to thereby permit the second DNA binding protein protein to regulate the expression of the target gene.

27. The method of claim 26 wherein said transcriptional regulatory protein is an activator.

28. The method of claim 26 wherein said transcriptional regulatory protein is a repressor.

29. The method of claim 26 wherein said target gene is a recombinant target gene.

30. The method of claim 26 wherein said cell is selected from the group consisting of plant, algae, fungi, yeast and animal cells.

31. The method of claim 30 wherein said animal cell is a mammalian cell.

32. The method of claim 31 wherein said mammalian cell is an isolated human cell.

33. The method of claim 26 wherein said chromophore is exogenously supplied.

* * * * *